US009175258B2

(12) United States Patent
Bywater-Ekegard et al.

(10) Patent No.: US 9,175,258 B2
(45) Date of Patent: Nov. 3, 2015

(54) MICROBIAL COMPOSITIONS AND METHODS

(75) Inventors: Margaret Bywater-Ekegard, Lac Brome (CA); Ananda Fitzsimmons, Lac Brome (CA)

(73) Assignee: Inocucor Technologies, Inc., Quebec (CA)

( * ) Notice: Subject to any disclaimer, the term of this patent is extended or adjusted under 35 U.S.C. 154(b) by 0 days.

(21) Appl. No.: 13/979,419

(22) PCT Filed: Jan. 12, 2012

(86) PCT No.: PCT/IB2012/000833
§ 371 (c)(1),
(2), (4) Date: Jan. 6, 2014

(87) PCT Pub. No.: WO2012/101528
PCT Pub. Date: Aug. 2, 2012

(65) Prior Publication Data
US 2014/0120601 A1 May 1, 2014

Related U.S. Application Data

(60) Provisional application No. 61/432,152, filed on Jan. 12, 2011.

(51) Int. Cl.
| | |
|---|---|
| *C12N 1/20* | (2006.01) |
| *C12N 1/18* | (2006.01) |
| *C12N 1/12* | (2006.01) |
| *C12N 1/14* | (2006.01) |
| *C12N 1/16* | (2006.01) |
| *C12R 1/125* | (2006.01) |
| *C12R 1/865* | (2006.01) |
| *A01N 63/04* | (2006.01) |
| *A01G 1/00* | (2006.01) |
| *C02F 3/34* | (2006.01) |

(52) U.S. Cl.
CPC *C12N 1/20* (2013.01); *A01G 1/001* (2013.01); *A01N 63/04* (2013.01); *C02F 3/34* (2013.01); *C02F 3/341* (2013.01); *C02F 3/347* (2013.01); *C12N 1/12* (2013.01); *C12N 1/14* (2013.01); *C12N 1/16* (2013.01); *C12R 1/125* (2013.01); *C12R 1/865* (2013.01); *Y02W 10/37* (2015.05)

(58) Field of Classification Search
None
See application file for complete search history.

(56) References Cited

U.S. PATENT DOCUMENTS

| | | | |
|---|---|---|---|
| 5,578,486 A | 11/1996 | Zhang | |
| 5,667,779 A | 9/1997 | Kubo | |
| 6,025,187 A | 2/2000 | Penaud | |
| 6,905,288 B2 | 6/2005 | Miyazaki | |
| 7,811,353 B2 | 10/2010 | Blais | |
| 2001/0014324 A1* | 8/2001 | Moesinger | 424/115 |
| 2012/0015806 A1 | 1/2012 | Paikray et al. | |
| 2012/0031157 A1 | 2/2012 | Paikray | |

FOREIGN PATENT DOCUMENTS

| | | |
|---|---|---|
| CN | 101698539 | 4/2010 |
| RU | 2322061 C2 * | 4/2008 |
| WO | WO 2011157747 A2 * | 12/2011 |

OTHER PUBLICATIONS

Mukherjee, A.K. and Bordoloi, N.K. "Bioremediation and reclamation of soil contaminated with petroleum oil hydrocarbons by exogenously seeded bacterial consortium: a pilot-scale study", Environmental Science and Pollution Research, Epub Sep. 2010, vol. 18, pp. 471-478.*
Bankar AV, et al. (2009) Environmental and industrial applications of Yarrowia lipolytica. *Applied Microbiology and Biotechnology*, 84(5): 847-865.
Bankar AV, et al. (2009) Removal of chromium (VI) ions from aqueous solution by adsorption into two marine isolates of Yarrowia lipolytica. *Journal of Hazardous Materials*, 170(1): 487-494.
Fickers P, et al. (2005) Hydrophobic substrate utilisation by the yeast Yarrowia lipolytica, and its potential applications. *FEMS Yeast Research*, 5(6-7): 527-543.
Harwood CS, et al. (1999) Anaerobic metabolism of aromatic compounds via the benzoyl-CoA pathway. *FEMS Microbiology Reviews*, 22: 439-458.
Nam, et al. (2003) A novel catabolic activity of *Pseudomonas veronii* in biotransformation of pentachlorophenol. *Applied Microbiology and Biotechnology*, 62(2-3): 284-290.
Onaca, et al. (2007) Degradation of alkyl methyl ketones by *Pseudomonas vernil*. *Journal of Bacteriology*, 189(10): 3759-3767.
Jain MR, et al. (2004) 2,4,6-trinitrotoluene transformation by a tropical marine yeast, Yarrowia liplytica NCIM 3589. *Marine Pollution Bulletin*, 49(9-10): 783-788.
Rokas A. (2009) The effect of domestication on the fungal proteome. *Trends in Genetics: TIG*, 25(2): 60-63.
Schennen U, et al. (1985) Anaerobic degradation of 2 fluorobenzoate by benzoate-degrading, denitrifying bacteria. *J. Bacteriol.*, 161(1): 321-325.
Taher DM, et al. (2009) Comparison of normal composting with composting using effective microorganisms for poultry carcasses disposal in poultry farms. *Iraqi Journal of Veterinary Sciences*, 23(2): 1607-3994.
International Preliminary Report on Patentability issued by the International Searching Authority on Jul. 16, 2013 for PCT/IB2012/000833 filed Jan. 12, 2012 and published as WO 2012/101528 on Aug. 2, 2012 (Applicants—Inocucor; Inventors—Bywater-Ekegard, et al.; (9 pages).

(Continued)

*Primary Examiner* — Allison Fox
*Assistant Examiner* — Michelle F Paguio Frising
(74) *Attorney, Agent, or Firm* — Ballard Spahr, LLP

(57) ABSTRACT

The present invention comprises compositions and methods for enhancing biological processes, such as plant growth or bioremediation. For example, the present invention comprises compositions and methods for effectively remediating chemical and organic wastes and reducing the environmental risk from manure, septic, sewage, oil pollution, and other contaminants.

12 Claims, 3 Drawing Sheets

(56) References Cited

OTHER PUBLICATIONS

International Search Report issued by the International Searching Authority on Aug. 10, 2012 for PCT/IB2012/000833 filed Jan. 12, 2012 and published as WO 2012/101528 on Aug. 2, 2012 (Applicants—Inocucor; Inventors—Bywater-Ekegard, et al.; (3 pages).

Written Opinion issued by the International Searching Authority on Aug. 10, 2012 for PCT/IB2012/000833 filed Jan. 12, 2012 ; and published as WO 2012/101528 on Aug. 2, 2012 (Applicants—Inocucor; Inventors—Bywater-Ekegard, et al.; (8 pages).

Harwood CS, et al. (1986) Uptake of Benzoate by *Rhodopseudomonas palustris* Grown Anaerobically in Light. *J. Bacteriology,* 165(2): 504-509.

Ying, Liu, et al., Review on Degradation and Conversion of Environmental Pollutants by Mycorrhizal Fungi. Shanghai Environmental Sciences, vol. 17, No. 2, pp. 127-131.

First Office Action issued by the State Intellectual Property Office of the People's Republic of China on Sep. 3, 2014 for Chinese Application No. 201280009159.9 filed on Jan. 12, 2012, which was published as 103649303A on Mar. 9, 2014 (Inventor—Bywater Ekegärd; Applicant—Inocucor).

First Examination Report issued by the Australian Patent Office on Mar. 18, 2015 for Australian Application No. 2012210260 filed on Jan. 12, 2012 (Inventor—Bywater Ekegärd; Applicant—Inocucor).

Second Office Action issued by the State Intellectual Property Office of the People's Republic of China on Jul. 14, 2015 for Chinese Application No. 201280009159.9, filed on Jan. 12, 2012, and published as 103649303A on Mar. 9, 2014 (Inventor—Bywater Ekegard; Applicant—Inocucor Tech., Inc.) (Translation—7 pages).

\* cited by examiner

| N° | ENZYMES | SUBSTRATS | pH | B.subtilis 0249 | B.subtilis EVL | L.plantarum | A.oryzae | Lc.lactis | R.palustris | C.utilis | S.cerevesiae INO |
|---|---|---|---|---|---|---|---|---|---|---|---|
| 1 | Témoin | | | - | - | | - | - | | - | - |
| 2 | Phosphatase alkaline | 2-naphtyl phosphate | 8.5 | ++ | ++ | | +++++ | +++++ | | ++++ | +++ |
| 3 | Estérase (C 4) | 2-naphtyl butyrate | 6.5 | +++ | +++ | | +++ | - | | +++ | ++ |
| 4 | Estérase Lipase (C 8) | 2-naphtyl caprylate | 7.5 | ++ | ++ | | +++ | - | | - | +++ |
| 5 | Lipase (C14) | 2-naphtyl myristate | | - | - | | - | - | | - | - |
| 6 | Leucine arylamidase | L-leucyl-2-naphtylamide | | +++ | ++++ | | +++++ | - | | ++++ | +++++ |
| 7 | Valine arylamidase | L-valyl-2-naphtylamide | | ++ | +++ | | ++ | - | | + | +++ |
| 8 | Cystine arylamidase | L-cystil-2-naphtylamide | | - | - | | - | - | | - | +++++ |
| 9 | Trypsine | N-benzoyl-DL-arginine-2-naphtylamide | 8.5 | - | - | | - | - | | - | - |
| 10 | α-chymotripsine | N-glutaryl-phénylalanine-2-naphtylamide | 7.5 | - | - | | - | - | | - | - |
| 11 | Phosphatase acide | 2-naphtyl phosphate | 5.4 | + | ++ | | +++++ | ++++ | | +++ | +++++ |
| 12 | Naphtol-AS-BI-phosphohydrolase | Naphtol-AS-BI-phosphate | | + | ++ | | +++ | - | | ++ | + |
| 13 | α-galactosidase | 6-Br-2-naphtyl-αD-galactopyranoside | | - | + | | - | - | | - | - |
| 14 | β-galactosidase | 2-naphtyl-βD-galactopyranoside | | - | +++++ | | - | - | | - | - |
| 15 | β-glucuronidase | Naphtol-AS-BI-βD-glucuronide | | - | - | | - | - | | - | - |
| 16 | α-glucosidase | 2-naphtyl-αD-glucopyranoside | | ++ | - | | ++++ | - | | - | ++++ |
| 17 | β-glucosidase | 6-Br-2-naphtyl-βD-glucopyranoside | | +++++ | - | | +++ | - | | - | +++ |
| 18 | N-acétyl-β-glucosaminidase | 1-naphtyl-N-acétyl-βD-glucosaminide | | - | - | | - | - | | - | - |
| 19 | α-mannosidase | 6-Br-2-naphtyl-αD-mannopyranoside | | - | - | | - | - | | ++ | - |
| 20 | α-fucosidase | 2-naphtyl-αL-fucopyranoside | | - | - | | - | - | | - | - |

FIGURE 1

MICROBIAL COMPOSITIONS AND METHODS

CROSS-REFERENCE TO RELATED APPLICATIONS

This application is a National Phase Application of International Application No. PCT/IB2012/000833 filed Jan. 12, 2012, which claims the benefit of priority of U.S. Provisional Patent Application Ser. No. 61/432,152, filed Jan. 12, 2011, each of which is herein incorporated reference in its entirety.

TECHNICAL FIELD

The present invention relates to compositions and methods comprising microorganisms, for example, for bioremediation. More particularly, the present invention comprises compositions and methods comprising microorganisms, such as bacterial mixtures, for various purposes. For example, effectively remediating soil and water sources and reduction of chemical and organic wastes and reducing the environmental risk from manure, septic, sewage, oil pollution, and other contaminants. Additionally, the compositions and methods of this invention can be used to sustainably manage soil and water, and repair ecosystems affected by contamination or pollution.

BACKGROUND OF THE INVENTION

Contaminants, such as hazardous, polluting, or toxic materials or wastes, are a health and safety problem for the United States and for countries world-wide. Governmental agencies, commercial companies, the military, and consumers are searching for more cost-effective technologies that can be used to remove these hazardous and polluting materials. Moreover, environmental regulations are mandating a change to sustainable management of soil and water contamination.

Contaminants are continuously produced by activities of humans on the planet. In addition, natural causes can release or create contaminants in the environment. Oil and radioactive elements are naturally released into the environment and natural disasters, such as floods, create polluted areas in their wake. In addition to the on-going production of waste materials, there is a large amount of contamination from human and natural activities in the past.

The costs of cleaning up the environment are staggering. These costs are a drain on the economies of thriving countries and are an almost insurmountable problem for poorer countries. Many of the current technologies for removing hazardous or contaminating wastes from the environment require transportation over long distances and involve sophisticated machinery or personnel, all of which add to the costs, environmental contamination, and do not support local communities.

Current methods of waste treatment are generally not adequate for remediating the contaminated air, soil or water. Chemical treatment can be used on some wastes, but there may be hazardous by-products, leachate or sludge produced by treatment. Wastes may be isolated or altered through methods such as stabilization, solidification or encapsulation. But, in these approaches the waste is merely contained, not destroyed or converted. Additionally, the problem of storage of the contained waste is created.

What is needed are compositions and methods that can perform bioremediation, such as at a contaminated or polluted site, or to remediate materials such as soil or water that have an excess of unwanted biological material or other contaminating or polluting compounds, or to enhance the health and sustainability of the local natural environment, that can be applied to a wide variety of environments. Even more ideally, would be a bioremediation system that would not only remove or stabilize the contaminated wastes, but would also be capable of converting some of the wastes into usable products. What is also needed are methods and compositions for enhancing biological processes, such as enhancing plant growth.

SUMMARY

The present invention comprises compositions and methods comprising microorganisms, such as bacteria, for example, for treatments of environments, for enhanced plant growth, reduction of contaminants, bioremediation, reduction of unwanted plant or microbial species, and production of natural products such as food supplements, nutriceuticals, cosmeceuticals cosmetics and pharmaceuticals. Compositions and methods of the present invention may comprise microorganism-containing compositions provided to an environment and/or microorganism-containing compositions attached, adhered to, or in close association with surfaces, wherein the surfaces can be living organisms, such as rhyzomes, rootlets and/or roots, or other plant or animal surfaces, or inert surfaces such as glass beads, shells, plant material, plastics, metal, wood, ceramics, and woven or nonwoven materials. The present invention comprises compositions and methods useful in the control and reduction of contamination and pollution in lentic water, such as contained bodies of water, including but not limited to lakes and ponds. The present invention comprises compositions and methods useful in the control and reduction of contamination and pollution in lotic water, such as flowing bodies of water.

The present invention comprises compositions and methods useful in the bioremediation of sites contaminated by hydrocarbons including, but not limited to, oil and organic solvents, wherein site may comprise solids, soils, liquids, bodies of water, or mixtures of solids and liquids.

The present invention comprises compositions and methods useful in ameliorating and cleansing hydrocarbon-contaminated wildlife. The present invention comprises compositions and methods useful in the bioremediation of soil.

The present invention comprises compositions and methods useful in the treatment or management of commercial, municipal and residential septic systems, and reduction of biosludge.

The present invention comprises compositions and methods useful in the treatment of municipal and industrial wastewater, the reduction of failures by treatment plants for municipal and industrial wastewater, and management of municipal or industrial wastewater. The present invention comprises compositions and methods useful in the recycling of water used in industrial, mining, commercial, private or individual processes.

The present invention comprises compositions and methods useful in the treatment of water contained by dams.

The present invention comprises compositions and methods useful in controlling odors generated by a site, and accelerating the microbial processes in composting facilities and for treating leachate from landfills.

The present invention comprises compositions and methods useful in the decontamination of soils contaminated by hydrocarbons, solvents, pathogenic microbial organisms, animal wastes or other organic wastes. The present invention comprises compositions and methods useful in the decontamination of soil and water, particularly contaminated soil or water resulting from natural disasters or from people living in unsanitary conditions without adequate waste control facilities.

The present invention comprises compositions and methods useful in the treatment of animal waste generated at facilities where animals are bred, raised, live or slaughtered, such as farms, and industrial farming complexes for example, dairy farms in the production of milk, chicken or egg production facilities, swine production facilities, pet boarding and sitting facilities, and other commercial or individual farms or animal containment sites.

The present invention comprises compositions and methods useful in the creation and maintenance of healthy soil environments. The present invention comprising compositions and methods useful to condition soil and maintain a balanced and sustainable soil ecology which can support the growth of plants, optionally with minimal chemical input. The present invention enhances plant growth, supports plant maturation and increased yields, rapid seed germination and increased biomass.

The present invention comprises compositions and methods useful in the remediation of mold, in contained environments, such as rooms or buildings, or in exterior locations such as on surfaces of buildings, and for example such compositions and methods may be used in an area that has been affected by flooding or in areas of high humidity.

The present invention comprises compositions and methods useful in improving the qualities of soil. The present invention comprises compositions and methods that aid in plant growth and enhance seed germination, root production, increased yield by plants, increased fruiting, prolonging production by plants either in a season or throughout the productive lifespan of the plants, and increased vigor and biomass of plants.

The present invention comprises compositions and methods useful in the control of insects and insect borne disease in plants. The present invention comprises compositions and methods useful in bee keeping.

The present invention comprises compositions and methods useful in the techniques of hydroponic or aeroponic agriculture or a controlled plant growing system combining hydroponic and aeroponic methods. The present invention comprises compositions and methods useful in aquaculture or pisciculture. The present invention comprises compositions and methods useful in the process of vertical farming.

The present invention comprises compositions and methods useful in the remediation of industrial by-products, such as by-products from the construction industry, for example, treated lumber, from nuclear wastes from any source including defense or hospital sources, and other industrial wastes that may be treated with the compositions of the present invention. The present invention comprises compositions and methods useful in the raising or keeping of animals.

The present invention comprises compositions and methods useful in the mining industry. The present invention comprises compositions and methods useful in the healthcare industry, for example by providing natural sources of products extracted or purified from plants or microbial compositions or a combination thereof, comprising food supplements, nutriceuticals, pharmaceuticals, cosmeceuticals and cosmetics. The present invention comprises compositions useful as additives in products for human or animal consumption or use.

The present invention comprises compositions and methods useful in domestic settings such as a household. The present invention comprises compositions and methods useful in a variety of nanotechnologies such as nanoparticle delivery of microorganism-containing compositions s or microorganisms described herein.

BRIEF DESCRIPTION OF THE FIGURES

FIG. 1 shows a chart of representative enzyme activity tests for certain bacteria.

DETAILED DESCRIPTION

Figure 2:
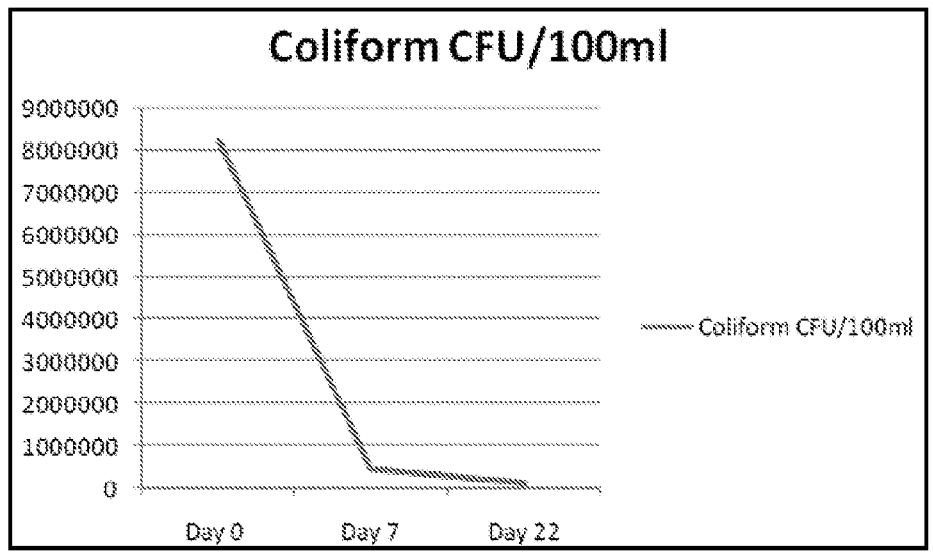
FIG. 2 is a graph showing a decrease in coliforms after treatment with a composition of the present invention.

The present invention comprises compositions and methods comprising microbial organisms, which may be used in methods including but not limited to, bioremediation and development and maintenance of healthy ecosystems. Compositions may comprise a mixture of microorganisms, comprising bacteria, fungi, algae, and/or other indigenous or exogenous microorganisms, all of which form a micro ecosystem with roles for its members. It is currently believed, though not wishing to be bound by any particular theory, that compositions and methods of the present invention enhance the naturally occurring mutual symbiosis between the feeding roots of the plants, soil fungi and soil bacteria. Compositions and methods of the present invention may comprise a mixture of isolated microorganisms, and may act as a vehicle and/or a delivery system for exogenous microorganisms and/or endogenous consortia of microorganisms.

Compositions and methods of the present invention may act in a paracrine and/or mutuality regenerative fashion to restore a polluted or contaminated environment's microorganisms and other flora. For example, in a composition of the present invention, one or more microorganisms may be capable of modifying or eliminating the polluting or contaminating compounds or molecules, one or more microorganisms may provide nutrition and promote healthy ecological processes, and one or more microorganisms may facilitate detoxification activities and regenerate the natural ecology. Microorganisms of the present invention may consume specific substances in the polluted environment, and produce metabolic by-products that act as nutrients for other microorganisms of the composition of the present invention as well as to the microorganisms existing in that environment. Compositions of the present invention may provide microorganisms that produce biological agents including but not limited to antibiotics or surfactants.

Compositions of the present invention comprise isolated microorganisms and compositions comprising isolated microorganisms. A composition of the present invention is a mixed culture of isolated microorganisms (referred to as IN-M1) that was deposited with the ATCC under the Budapest Treaty, on Jan. 12, 2011, under Account No. 200139, and given Accession Number PTA-12383. This composition comprises isolated microorganisms *Rhodopseudomonas palustris, Bacillus subtilis, Saccharomyces cerevisiae, Aspergillus oryzae, Lactobacillus helveticus* and *Lactobacillus caseii*. Compositions of the present invention comprise compositions comprising one or more isolated microorganisms. For example, a composition may comprise *Rhodopseudomonas palustris, Bacillus subtilis, Pseudomo-* nas aeruginosa, Saccharomyces cerevisiae, Aspergillus oryzae, Candida utilis, Streptococcus lactis, Lactobacillus planterum, Lactobacillus helveticus, and Lactobacillus caseii. For example, a composition may comprise the isolated microorganism Lactobacillus helveticus, referred to herein as IN-LH1, which was deposited with the ATCC under the Budapest Treaty, on Jan. 12, 2011, under Account No. 200139, and given Accession Number. PTA-12386. A composition may comprise the isolated microorganism Bacillus subtilis, referred to herein as IN-BS1, which was deposited with the ATCC under the Budapest Treaty, on Jan. 12, 2011, under Account No. 200139, and given Accession Number. PTA12385. A composition may comprise the isolated microorganism Saccharomyces cerevisiae, referred to herein as IN-SC1, which was deposited with the ATCC under the Budapest Treaty, on Jan. 12, 2011, under Account No. 200139, and given Accession Number. PTA-12384. A composition may comprise the isolated microorganism Rhodopseudomonas palustris, referred to herein as IN-RP1, which was deposited with the ATCC under the Budapest Treaty, on Jan. 12, 2011, under Account No. 200139, and given Accession Number. PTA-12387. A composition of the present invention may comprise a mixture of isolated microorganisms comprising one or more of Lactobacillus helveticus, referred to herein as IN-LH1 (Accession No. PTA-12386), Bacillus subtilis, referred to herein as IN-BS1 (Accession No. PTA-12385), Saccharomyces cerevisiae, referred to herein as IN-SC1 (Accession No. PTA-12384), Rhodopseudomonas palustris, referred to herein as IN-RP1 (Accession No. PTA-12387). Examples of isolated microorganisms in compositions of the present invention include, but are not limited to, Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus, and/or Lactobacillus caseii. Compositions of the present invention may comprise differing amounts and combinations of these and other isolated microorganisms depending on the methods being performed. Compositions of the present invention are useful in the methods taught herein.

Isolated microorganisms that are useful in compositions and methods of the present invention include, but are not limited to, one or more of the following:

| Microorganisms | |
|---|---|
| Lactobacillus | Hyperthermophile |
| Lactobacillus fermentum | Methanopyrus. kandleri |
| Streptococcus thermophilus | Methanobrevibacter smithii |
| Lactococcus diacetyllactis | Pyrococcus furiosus |
| Lactococcus lactis | Ferrglobus |
| Bifidobacterium bifidum | Ferrglobus placidus |
| Lactibacillus delbruecki | Hydrothermal |
| Yeasts | Pyrolobus fumarii |
| Candida antarctica | Thermophile |
| Candida chauliode | Sulfolobus acidocaldarius |
| Candida corydali | Sulfolobus islandicus |
| Candida albicans | Sulfolobus metallicus |
| Lodderomyces elongisporus. | Sulfolobus shibatae |
| Candida dosseyi | Sulfolobus solfataricus |
| Candida blattae | Bacillus thuringiensis |
| Candida ascalaphidarum | Bacillus thuringiensisIsraelensis |
| Candida membranifaciens | Pseudomonas |
| Candida oleophila | Pseudomonas alcaligenes |
| Streptomyces albus | Pseudomonas mendocina |
| Lachancea fermentati, | Pseudomonas pseudoalcaligenes |
| Lachancea thermotolerans | Pseudomonas resinovorans |
| Hanseniaspora vineae | Pseudomonas veronii |
| Saccharomycotina | Pseudomonas putida |
| Aspergillus | Pseudomonas stutzeri |

-continued

| Microorganisms | |
|---|---|
| Aspergillus oryzae | Pseudomonas fluorescens |
| Aspergillus niger | Pseudomonas chlororaphis |
| Aspergillus terreus | Pseudomonas aurantiaca |
| Aspergillus fischerianus | Pseudomonas aeruginosa, |
| Green sulfur bacteria | White rot fungi |
| Purple sulfur bacteria | Xanthomonas |
| Chromatiaceae | Acinetobacter |
| Ectothiorhodospiraceae, | Rhodococcus sp. |
| Halothiobacillaceae | Arthrobacter |
| Halothiobacillus halophilus | Aureobasidium sp. |
| Halothiobacillus hydrothermalis | Alcaligeness sp. |
| Halothiobacillus kellyi | Leuconostoc sp. |
| Halothiobacillus neapolitanus | Sclerotium sp. |
| Purple non sulfur bacteria | Clostridium, |
| Rhodopseudomonas palustris | Zymomonas |
| Salt or Ocean Bacterium | Klebsiella |
| Halobacterium jilantaiense | Micorrhizal fungi |
| Halobacterium noricense | |
| Halobacterium salinarum | |
| Halobacterium piscisalsi | |

The present invention comprises isolated microorganisms. For example, an isolated microorganism of the present invention is Lactobacillus helveticus, referred to herein as IN-LH1, which was deposited with the ATCC under the Budapest Treaty, under Account No. 200139, and given Accession Number. PTA-12386. An isolated microorganism of the present invention is Bacillus subtilis, referred to herein as IN-BS1, which was deposited with the ATCC under the Budapest Treaty, under Account No. 200139, and given Accession Number. PTA-12385. An isolated microorganism of the present invention is Saccharomyces cerevisiae, referred to herein as IN-SC1, which was deposited with the ATCC under the Budapest Treaty, under Account No. 200139, and given Accession Number. No. PTA-12384. An isolated microorganism Rhodopseudomonas palustris, referred to as IN-RP1, which was deposited with the ATCC under the Budapest Treaty, under Account No. 200139, and given Accession Number. PTA-12387.

In an aspect, the isolated microorganisms of the present invention can be grown in large, industrial scale quantities. For example, and not to be limiting, a method for growing microorganisms in 1000 liter batches comprises media comprising 30-70 liters of non-sulphur agricultural molasses, 2-5 liters of wheat bran (0.02-0.05% by volume), 2-5 liters of kelp (0.02-0.05% by volume), 2-5 liters of bentonite clay (0.02-0.05% by volume), 0.5 to 3 (0.005-0.03% by volume) liters fish emulsion (a commercially available organic soil amendment, from Nutrivert, Dunham, Quebec non-pasteurized), 0.5 to 3 liters soy flour (0.005-0.03% by volume), 0.4 to 1.5 mg of commercially available sea salt, and 20-70 liters total of selected strains of isolated microorganisms at $1 \times 10^5$ to $1 \times 10^7$ cells/mL, for example, Lactobacillus helveticus, (IN-LH1, Accession Number. PTA-12386), Bacillus subtilis, (IN-BS1, Accession Number PTA-12385), Saccharomyces cerevisiae, (IN-SC1, Accession Number. PTA-12384), Rhodopseudomonas palustris, (IN-RP1 Accession Number. PTA-12387), or a mixed culture, N-M1 Accession Number. PTA-12383.

The total is brought to 1000 liters in non-chlorinated warm water. A method for growing the microorganisms may comprise dissolving molasses in some of the warm water, adding the other ingredients to the fill tank, adding the desired bacteria, keeping the temperature between 28-35° C., and, after the pH drops to about 3.5-4.0, usually within several days, with stirring lightly and monitoring of pH. The culture can incubate for weeks, typically from 5 to 10 weeks, and may be bottled, or stored, resulting in a composition of the present invention. The composition may be bottled and stored, for example in airtight containers out of sunlight at room temperature. In one aspect, the culturing method and composition may include samples of a pollutant or pollutants from an environment to be remediated or restored, and optionally, the sample may include indigenous microorganisms from the polluted environment. Compositions may comprise one or a consortium of endogenous microorganisms isolated from the environment to be treated and/or remediated.

The term, "remediation" as used herein, is the act or process of correcting a fault or deficiency, such as in modulating, ameliorating, reducing, reversing or stopping environmental damage. In the case of environmental remediation, it is acting on contaminants, such as hazardous or polluting materials, which may be changed chemically, or physically, or stabilized or sequestered or in some other way removed from the surrounding environment. Remediation may comprise reduction of phosphates and may include the combination compositions of the present invention with plants, endogenous and exogenous natural microorganisms and animalia. Bioremediation, as used herein, means using biological organisms, alone or in conjunction with inert structures, as a system for treating, modulating or altering the contaminants, such as hazardous or polluting materials.

Contaminant, as used herein, means any molecules, chemicals or organisms in the environment that are harmful to other living organisms in the environment or to the abiotic elements of the environment, and includes compounds or molecules that are in an amount greater than is desired for that environment even if such compounds or molecules are not inherently harmful if found in lower amounts, and the term may be used interchangeably with the term "pollutant". Biological, chemical, physical, or radiological substance (normally absent in the environment) which, in sufficient concentration, can adversely affect living organisms through air, water, soil, and/or food are included in the terms contaminant or pollutant. The term, "toxic materials" as used herein, is included in the term contaminant. The contaminants may also be a natural element of the environment that is present in such a concentration that it is now harmful to the environment and its constituents. The contaminant may be an element that has been introduced into the environment by human activities, such as synthesis of the material, or by natural causes. The term contaminant, as used herein, encompasses the presence of one or more toxic, hazardous, or polluting materials in an area.

Contaminant, as used herein, also means any molecules, chemicals or organisms in the environment that are present in an undesired concentration or amount. The contaminant may not necessarily be harming any component of the environment but may be present in an undesired quantity.

The term, "environment" as used herein, is defined generally as the site, surroundings or conditions in which a person, animal, or plant lives or operates, and more specifically in terms of remediation as an area as defined by the contaminant situation, and environment may include the biotic and abiotic elements, and the patterns of the interrelationships between the biotic elements, and between the biotic and abiotic elements which are found in the defined area. All three physical states, solids, liquids and gases, may be included in the elements that make up the environment.

As used herein, microorganism include, but are not limited to, bacteria, viruses, fungi, algae, yeasts, protozoa, worms, spirochetes, single-celled and multi-celled organisms that are included in classification schema as prokaryotes, eucaryotes, Archea, Bacteria and those that are known to those skilled in the art. Microorganisms may also refer to isolated microorganisms and may comprise particular deposited compositions or microorganisms disclosed herein, and the intent of the text can be interpreted by those of skill in the art.

The compositions of the present invention comprise a combination of isolated microorganisms from several genera and/or species. These isolated microorganisms grow and live in a cooperative fashion, in that some genera or species may provide by products or synthesized compounds that are beneficial to other microorganisms in the combination. In making a mixed culture, individual characteristics of one or more isolated microorganisms are used to select a microorganism for inclusion in the mixed culture. For example, characteristics may include, but are not limited to, enzymes made by the microorganism, the ability to supplement another microorganism's metabolism, growth or other activities; the ability to complement the metabolic or enzymatic pathways of other microorganisms in the mixed culture, non-spore formation, ability to survive, replicate or metabolize in adverse media or conditions, oxygen consumption, ability to use energy sources such as light or chemicals other than carbon, the lack of predation on other microorganisms in the mixed culture, the ability to provide environmental aspects, such as structures (by, for example, producing hyphae, cellular extensions, pilli, or forming a slime or biofilm layer on structures in the environment), pH, reducing or enhancing oxygen levels, carbon dioxide levels, or other metabolic needs, and other activities known to be made by one microorganism that can be used by microorganisms in the mixture. Those of skill in the art in the microbial arts are well aware of such characteristics of microorganisms. One or more mixed cultures may be used in compositions and methods of the present invention, for example, IN-M1, or compositions comprising IN-LH1, IN-BS1, IN-SC1, and/or IN-RP1, in combination or individually, and/or with other isolated microorganisms, such as those isolated from a site to be treated or sites similar to those to be treated.

For example, in a composition of the present invention, both aerobic microorganisms, which need oxygen for metabolic activities, and anaerobic microorganisms, which use other sources of energy such as sunlight or the presence of specific substrates, are combined to form a composition. This enables the composition's isolated microorganisms to colonize substrates in different regions of an environment. For example, one or more mixed cultures may be used in compositions and methods of the present invention, for example, IN-M1, or compositions comprising IN-LH1, IN-BS1, IN-SC1, and/or IN-RP1, in combination or individually, and/or with other microorganisms.

A composition may comprise facultative microorganisms, for example, strains of *lactobacillus*, which modulate metabolic activities according to oxygen and/or nutrient concentrations in the environment. Though not wishing to be bound by any particular theory, it is currently believed facultative microorganisms in a composition provide a prolonged shelf-life at room temperature for a composition of the present invention. For example facultative microorganisms such as IN-BS1 or IN-LH1 may be included in compositions and methods described herein.

All species of living organisms include individual organisms that vary genetically and biochemically from each other but are still within what is called the spectrum of normal variations within the species. These individual natural variations may be the result of nondisruptive substitution or deletions in the gene sequence, variation in gene expression or RNA processing and/or variations in peptide synthesis and/or variation of cellular processing of intra cellular, membrane or secreted molecules. Compositions of the present invention may comprise microorganisms that are within or without the normal variations of a species. Identification of such microorganisms may be detected by genetic, molecular biological methods known to those skilled in the art, and/or by methods of biochemical testing.

For example, a composition of the present invention comprises isolated microorganisms selected by isolating individual colonies of a particular microorganism. The colony members were characterized, for example, by one or more characteristics, such as by testing enzyme levels present in the isolated microorganism and the activity with particular substrates in a panel of substrates, to establish an enzyme profile for the isolated microorganism. These substrates are representative of a cross-section of the biochemical pathways needed by the microorganisms in a composition of the present invention that is to be used in for general remediation purposes, such as the breakdown of organic matter of vegetable or animal matter, or for specific remediation purposes, such as the breakdown of particular chemicals. One or more selection criteria (characteristics of a microorganism) enable the formulation of compositions of isolated microorganisms that provide a standardized ecosystem that is ready to colonize an environment and to carry out particular reactions. For example, one characteristics is enzymes and activity of enzymes in microorganisms, such that all of the microorganisms that provide enzymes were tested for enzyme activity levels for substrates, enzyme profile testing. Microorganisms having compatible enzyme profiles may be combined to provide a composition for methods disclosed herein. Complementary enzyme profiles means that the enzyme profile of one microorganism is different from the enzyme profile of another microorganism, for example, one microorganism has fatase activity and another does not, or one microorganism providing an enzyme in a metabolic pathway that is lacking in another organism, or one microorganism have cellulase activity of +5 and another microorganism having a cellulase activity of +3 or +4.

An example of an enzyme profile test comprises providing substrates and noting where there is high activity, +3 or greater, and where there is little to no activity, +2 and below. For example, a *lactobacillus* was tested and had a +5 enzyme level for alkaline phosphatase and a 0 for lipase. Such a *lactobacillus* may be admixed in a composition of the present invention with another microorganism where the lipase production is +4 or +5. For example, a *lactobacillus* such as IN-LH1 may be used. Both enzyme activities may be desired in compositions where reactions are needed to breakdown organic matter, for example. Using microorganisms with differing characteristics allows for cooperative, completion of metabolic pathways in order not to have incomplete biochemical pathways which leave, either intermediary compounds that are not bioavailable to the environment, or are not available to other microbial species as nutrition or prebiotics, or that do not provide active compounds/enzymes targeting specific pollutants. Incomplete biochemical pathways also do not provide molecules involved in the production or activation of nutritional elements for different species in the composition or in the inoculated environment; hormones, growth factors, anti bactericides etc. with paracrine influence on the growth and regeneration of the damaged environment. Another detrimental effect of incomplete biochemical pathways are the production of intermediary compounds that are ether toxic and/or odorous, like hydrogen sulfide.

An example of an enzyme profile test for isolated microorganisms of the present invention is shown in FIG. 1.

For example, bacterial strains isolated from *Bacillus* species were characterized by enzyme profiles comprising ability to hydrolyze fibrous matter (cellulose and hemi cellulose), proteins and fat; and ability to complete the degradation of numerous intermediary molecules and cells that accumulate during the metabolic processes. These characteristics are useful for degradation of organic matter and reduction or prevention of odors and other gas emissions. On a scale of 0 to 5, by trained eyes in assessing the color change in the enzyme reaction, the ranking +4 to +5 are generally optimal, though lower responses by particular organisms may be acceptable. For example, a deposited culture of *Bacillus subtilis* IN-BS1, may be used as described herein.

The enzyme tests are commercially available and the testing procedures for microorganisms and methods for determining activity levels are well known in the art. Other characteristics include, for example, screening a yeast, such as *Saccharomyces cerevisiae* for fermentation enzymes and *Bacillus* species with known enzyme profiles. For example, a deposited culture of *Saccharomyces cerevisiae* microorganism, IN-SC1, may be used as described herein. Testing microorganisms to determine which strains have high enzyme activity of certain enzymes which take part in proven fermentation pathways allows for identification of microorganisms that will perform well in compositions used in methods for digesting organic components in food and which can use the available nutrients of organic origin; Isolation of individual colonies and the enzyme profile testing of these allows for the isolation of strong expressers of the enzymes. Additionally, using a combination of microorganisms that provide complimentary characteristics allows for complete degradation of organic matter, even in a cross-species manner. Though not wishing to be bound by any particular theory, it is believed that in the environment, as in higher organisms including humans, both one-way and two-way interactions between different cells may contribute to complex networks of interdependencies in microbial ecosystems.

Also not wishing to be bound by any particular theory, it is believed that identifying and using microorganisms that provide complementary or compatible profiles, such as enzyme profiles or other activities, allows for the inclusion of species that are indigenous to a site that is treated by the present invention. Other functional screening tests can be used to characterize indigenous complementary or compatible characteristics criteria for compositions that are used in remediation of particular pollutants and for the identification of other indigenous microorganisms.

An aspect of microorganisms which may be included in compositions of the present invention may be the characteristic of the formation or lack of formation of spores (nonsporulation). For example, bacterial isolates may be selected based on their response when moved from a starvation media to a nutrient rich media. isolates that show aggressive growth when transferred from a starvation medium to nutrient rich medium, and that also showed decreased sporulation, or a lower amount of spore formation in the starved cultures, are sometimes optimal for compositions. A species that survive adverse conditions by forming spores may or may not be optimal for compositions of the present invention. For example, species that sporulate less and rest in a vegetative state in adverse environments and then show aggressive growth in numbers in optimal environments may be more beneficial in compositions for remediating organic wastes and other contaminants.

An aspect of a characteristic for selection of microorganisms which may be included in a composition of the present invention is growth of the microorganism at different temperatures. For example, a *Bacillus* strain may be selected based on its ability to grow at different temperatures in aerobic conditions. Growth curves numbers of bacteria by OD and pH over time at different temperatures from 15 C-40 C may be used as an aspect for selection. Selected strains may be capable of growth in the presence of nitrates, capable of growth under anaerobic conditions or have other selected characteristics. For example, a *Bacillus* or purple non sulfur bacteria useful in methods and compositions of the present invention is characterized by the following: a +5 level of cellulase, a +2 to +3 level of proteinase, at least a +4 of fatase, grows in an 8% nitrate media, grows in a range of temperatures from 30° C. to 40° C., and does not form spores. For example, deposited cultures IN-BS1 and/or IN-RP1 that comprise *bacillus* and purple non sulfur bacteria microorganisms, respectively, are used as described herein.

*B. subtilis* will grow anaerobically, either by using nitrate or nitrite as a terminal electron acceptor, or by fermentation. A two-component signal transduction system is an early stage in the regulatory pathway governing anaerobic respiration. One of the essential roles of ResD and ResE in anaerobic gene regulation is induction of fnr transcription upon oxygen limitation. FNR is a transcriptional activator for anaerobically induced genes, including those for respiratory nitrate reductase, narGHJI. *B. subtilis* has two distinct nitrate reductases, one for the assimilation of nitrate nitrogen and the other for nitrate respiration. In contrast, one nitrite reductase functions both in nitrite nitrogen assimilation and nitrite respiration. Unlike many anaerobes, which use pyruvate formatelyase, *B. subtilis* can carry out fermentation in the absence of external electron acceptors wherein pyruvate dehydrogenase is utilized to metabolize pyruvate. *B. subtilis* generally grows at 25-37° C., gene expression observed at 15° C.-40° C. For example, deposited cultures that comprise a *B. subtilis*, IN-BS1 with ATCC number PTA-12385 are used as described herein.

Methods for selection of a microorganism for compositions described herein comprise determining characteristics of microbial isolates and establishing a profile of the characteristics for each isolate, such as by testing for enzyme profile activity, growth characteristics under differing conditions such as oxygen levels or temperature, growth in particular media conditions, such as nitrates, carbohydrates, minerals or particular contaminants, and characteristic responses for particular microorganisms, such as the ability to form spores or the ability to grow in the presence of pollutants or contaminants. Such tests of microbial characteristics are known in the art and any known tests are contemplated by the present invention. These tests allow for the characterization of a particular microorganism, the establishment of a profile of the characteristics of a particular microorganism, and a method of making a useful composition of the present invention comprises selecting microorganisms that are compatible individual species, based on their individual characteristics and how they interact together in a mixture. For example, two microbes are complementary when each one's characteristic profile is different in at least one characteristic from that of the other microbe, or complementary may comprise wherein a characteristic of one microbe is beneficial to or interactive with a characteristic of a second microbes or other microbes in the mixture. As used herein, compatible may mean that microorganisms can generally coexist in a composition. One testing criteria (characteristic) for microorganisms of the present invention in making a mixed culture is the interaction of the various species together. A microorganism may have the enzyme profile, or other tests and other characteristic criteria to make it compatible with at least one other microbe, but the first microorganism may not be able to grow well when added to a consortium of microorganisms, and thus that microorganism would not be selected as a component of a mixed culture composition of the present invention. Characteristics disclosed herein may be used to select individual microorganisms, or may be used to characterize a mixed culture of microorganisms as to the suitability of the mixed culture.

As used herein a microorganism does not mean one individual microorganism but a population or plurality of identical microorganism, such as a colony of *B. subtilis*. A mixture of microorganisms is a mixture of different microorganisms, such as *B. subtilis, L. helviticus, L. casei*, and a mixture may comprise different species, strains, genera, types, or other recognized ways of classifying, separating or identifying microorganisms.

Selection criteria of oxygen metabolism and nutrient concentrations may be used to characterize microorganisms in a composition of the present invention. For example, *Lactobacillus* strains may be selected based on the ability to modulate metabolic activity depending on the oxygen concentration or nutrient concentration in the growth media, and by extension, what activities the lactobacilli will have in a particular environment when used in a composition of the present invention. For example, *Lactobacillus* convert lactose and other sugars to lactic acid. The production of lactic acid makes the *lactobacillus* environment acidic, which inhibits the growth of some harmful bacteria. The majority of acidifying flora in the culture generally control the pH of the environment. This characteristic allows for methods of the present invention, when remediating an environment, to provide an environment with low pH without having to provide a very high volume of a composition. Such compositions can provide high concentrations of the acidifying microorganisms and provide a composition that has a greater than two years shelf life. In certain *Lactobacillus* strains, for example, *L. planterum*, the secretion of lactic acid is down regulated when the pH is below a pH 3 and up regulated when the pH is too high, whereas pH 4-5 is optimal.

*Lactobacillus* strains for a composition of the present invention may be selected on the basis of their ability to help provide the components in the formulation that provide stability for a prolonged shelf-life at room temperature. For example, if a composition of the present invention is stored in a sealed or closed container at room temperature, the biological activity of that composition is measured by opening the container and reactivation of the composition by known microorganism steps of dilution and the addition of molasses (a nutrient source) and incubation at 30-37° C. This is monitored by observing the pH going down to 3.7 and below in 5-7 days. A sealed container of a composition of the present invention, stored at room temperature, has a shelf life of longer than 2 months, longer than 4 months, longer than 6 months, longer than 8 months, longer than 10 months, longer than 1 year, or one year or longer. For example, deposited cultures that comprise *Lactobacillus* species, IN-LH1 with ATCC number PTA-12386 are used as described herein.

Beneficial yeasts, fungi and aspergillum provide nutrition, secreted enzymes and a network which provides filamentous structures in soil and which provide a structure to water or other liquids for biological components of a composition and the endogenous bacteria. Beneficial yeasts are those yeasts that are not pathogenic to plants or animals. Though not wishing to be bound by any particular theory, it is believe that providing structure, as mycelium does, increases the ability of the various species to find their preferred environment in the remediation environment and maximize their colonization and bioactivity. In a composition of the present invention, yeasts, fungi and aspergillum provide filamentous structures for the components to populate and cell debris to maintain the anaerobic photosynthetic bacteria present in the formulation.

A characteristic for yeast or micorrhyzi fungus that may be important in particular uses of compositions of the present invention is that they are nonpathogenic and nontoxic to humans and animals. It is known that mycelium in soil is important for aeration and that it excretes exoenzymes that breakdown organic nutritional sources for the fungi and that are used by the microbes in the environment. Fungi bind heavy metals such as cesium and other elements and are known to be useful in the purification of water flowing through the mycelium. It is believed that the mycelium attract symbionts (*Bacillus* sp., *Pseudomonas* sp. etc) in the environment and provide a fibrous network to colonize in a coexistence and providing an exocellular cooperative source of nutrients. For example, compositions that comprise yeast such as IN-SC1 or species expressing an enzyme system that includes cytochrome P450 protein or domain and/or fusaric acid or soil micorrhizal fungi are used as described herein.

The present invention comprises compositions comprising photosynthetic bacteria. For example, *R. palastrus*, such as IN-RP1 (Accession No. PTA-12387) may be a component of a composition based on its ability to scavenge organic waste, toxins and hydrocarbons. Phototropic bacteria may be components of compositions of the present invention. Purple sulfur or nonsulfur bacteria may be used in the compositions of the present invention. For example, compositions that comprise photosynthetic bacteria, IN-RP1 with ATCC number PTA-12387 are used as described herein.

Compositions of the present invention comprise bacteria and other microorganisms, such as those shown in Table 1. Bacteria which may be useful in the present invention include, but are not limited to the following. *Bacillus alcalophilus, Bacillus alvei, Bacillus amyloliquefaciens, Bacillus aneurinolyticus, Bacillus aquaemaris, Bacillus brevis, Bacillus caldolyticus, Bacillus centrosporus, Bacillus cereus, Bacillus circulans, Bacillus clausii, Bacillus coagulans, Bacillus firmus, Bacillus flavothermus, Bacillus fusiformis, Bacillus globigii, Bacillus halodurans, Bacillus infernos, Bacillus larvae, Bacillus laterosporus, Bacillus lentus, Bacillus licheniformis, Bacillus megaterium, Bacillus mesentericus, Bacillus mucilaginosus, Bacillus mycoides, Bacillus natto, Bacillus pantothenticus, Bacillus polymyxa, Bacillus pseudoanthracis, Bacillus pumilus, Bacillus schlegelii, Bacillus sphaericus, Bacillus sporothermodurans, Bacillus stearothermophilus, Bacillus subtilis, Bacillus thermoglucosidasius, Bacillus thuringiensis, Bacillus vulgatis,* and *Bacillus weihenstephanensis.*

The present invention comprises compositions and methods useful in the control and reduction of contamination and pollution in lakes and ponds. More specifically, the present invention comprises compositions and methods useful in the control and reduction of pond sludge. As used herein, "pond sludge" can mean algae, duckweed, or any other organic matter on the surface of the pond or underneath the surface of the pond. The compositions may comprise a blend of beneficial bacteria, yeasts and fermentation products, selected to grow with a particular species of microorganism, for example, *bacillus* species, and to enhance the growth or activities of natural microbes present in biological and organic waste and the surrounding environment. Compositions for control and reduction of contamination or pollution in lakes and ponds may comprise one or more mixed cultures used in compositions and methods of the present invention, for example, IN-M1, and/or compositions comprising IN-LH1, IN-BS1, IN-SC1, and/or IN-RP1, in combination or individually, and/or with other microorganisms.

The compositions may be a concentrated solution of microorganisms, for example, $1 \times 10^9$ cells per L, and can either be used as a concentrate, or diluted, for example at a rate of from about $1 \times 10^1$ to about $1 \times 10^4$, and sprayed on the surface and edges of the body of water or simply activated (placed in nutrient media and allowed to grow from an aliquot of a concentrated solution diluted in media) in an activation center (container). An activation center is one or more containers for growing a composition. A sealed or closed container of a composition is provided to a treatment location and the container is opened, the composition may be diluted into a media in an activation container or containers and the microorganisms are grown in media at 30°-37° C. for several days, such as 5-7 days, or until the pH is measured at pH 4, or 3.7, or below. This activation of the composition does not need to be performed under sterile or clean conditions, and it is beneficial if it is done on site where the remediation will take place. This is beneficial for water treatment methods. An activation center can be used, for example, for batches of 200-1000 liters and can be a modular design that can easily be expanded to increase activation capacity. The modules may be 200-1000 liters in size and multiple modules may be used to activate a composition. Activation of a composition is not limited to use of an activation container, and the composition may be grown in any container of a size needed to adequately allow the microorganisms in the composition to reproduce and survive.

In one aspect, the method of activation comprises 1) closing the valve on the activation container, 2) putting 10 liters of media into the container, 3) adding 20 liters of water, 4) adding 10 liters of the microorganism composition, 5) filling the activation container with additional water to the 200 liter mark, 6) heating to 30°-37° C.) leaving for 7-10 days, 8) testing the pH, and 9) using the activated composition, for example for application to a site once the pH is at or below 3.7. In one aspect, the bodies of water can be interconnecting shallow ponds. In one aspect, the compositions and methods are useful in the control of odor resulting from the accumulation of sludge at the bottom of a body of water. Methods of treating lentic water, such as ponds, lakes or contained bodies of water comprise methods of using a microorganism-containing composition comprising applying an effective amount of a microorganism-containing composition to lentic water or a contained body of water, allowing the composition to remain for a time period, for example time to grow and reproduce at the treated site, and reducing or eliminating at least a portion of the polluting or contaminating materials.

The present invention comprises compositions and methods useful in the control and reduction of contamination and pollution in flowing bodies of water such as rivers, streams, underground aquifers or underground streams. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii.* Microorganism-containing compositions may comprise one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition may comprise IN-M1, Accession No. PTA-12383. Methods of using a microorganism-containing composition comprise applying an effective amount of a microorganism-containing composition to flowing water, allowing the composition to remain for a time period, for example time to grow and reproduce at the treated site or in the flowing water, and reducing or eliminating at least a portion of the polluting or contaminating materials. Methods of using a microorganism-containing composition to treat flowing water may comprise providing a structure comprising an attached or a contained microorganism-containing composition such that the flowing fluid contact the immobilized microorganism-containing composition, having the microorganisms act on the flowing fluid, and reducing or eliminating one or more polluting or contaminating materials in the flowing fluid or lotic water.

The present invention comprises compositions and methods useful in the remediation of sites contaminated by hydrocarbons and/or heavy metals and/or unwanted bacteria such as E. coli. In one aspect, the compositions can be used to convert toxic hydrocarbons into harmless compounds of nitrogen, carbon dioxide, and water. Compositions may comprise a microorganism-containing composition wherein the microorganisms comprise Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus and Lactobacillus caseii. For example, a concentrated composition as taught in Example 1 may be used. Microorganism-containing compositions may comprise one or more mixed cultures, for example, IN-M1, or compositions comprising IN-LH1, IN-BS1, IN-SC1, and/or IN-RP1, in combination or individually, and/or with other microorganisms. For example, a microorganism-containing composition may comprise IN-M1, Accession No. PTA-12383. Methods of using a microorganism-containing composition comprise applying an effective amount of a microorganism-containing composition to a site or container comprising hydrocarbons and/or heavy metals and/or E. coli. allowing the composition to remain for a time period, for example time to grow and reproduce at the treated site or surface, and reducing or eliminating at least a portion of the hydrocarbons and/or heavy metals and/or microorganisms such as E. coli.

The present invention comprises compositions and methods useful in the mining industry, In one aspect the compositions and methods can be used to clean or treat mine tailings. In one aspect the compositions and methods can be used to clean or treat wastewater generated by mining. Compositions may be delivered using existing equipment, in fresh water, salt water or briny conditions, aerobic and anaerobic conditions and interfacing with existing infrastructure, existing and new aeration, mixing separation and monitoring systems used in the treatment or management of contaminated water, sludge, soil and mixtures thereof. Compositions may comprise a microorganism-containing composition wherein the microorganisms comprise Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus and Lactobacillus caseii. For example, a concentrated composition as taught in Example 1 may be used. Microorganism-containing compositions may comprise one or more mixed cultures, for example, IN-M1, or compositions comprising IN-LH1, IN-BS1, IN-SC1, and/or IN-RP1, in combination or individually, and/or with other microorganisms. For example, a microorganism-containing composition may comprise IN-M1, Accession No. PTA-12383. Methods of using a microorganism-containing composition comprise applying an effective amount of a microorganism-containing composition to a site or container comprising contaminants resulting from mining activities, allowing the composition to remain for a time period, for example time to grow and reproduce at the treated site or surface, and reducing or eliminating at least a portion of the contaminants resulting from mining activities, such as mine tailings, waste waters, soils or equipment.

The present invention comprises compositions and methods useful in the bioremediation of sites, containers or water sources contaminated by hydrocarbons, such as oil. In one aspect the contamination can result from an oil spill. Compositions of the present invention may comprise microorganisms that process hydrocarbons and nutrients which can stimulate the growth of microorganisms in the polluted environment to aid in reestablishment plant life in the affected environment and to protect marine and other wildlife that may be affected by the oil spill. Compositions comprising microorganisms may degrade hydrocarbons and other pollutants found at oil spill sites, like organic solvents, and may do so even in the presence of chemicals like surfactants. A method of the present invention may comprise applying or providing microorganism-containing compositions comprising oil degrading microbial organisms to a site contaminated by oil or other hydrocarbons, allowing the composition to remain for a time period, for example time to grow and reproduce at the treated site or surface, and removing at least a portion of the oil or hydrocarbons present. Compositions may comprise microorganisms adapted to degrade hydrocarbons, for example, isolated microorganisms that were isolated from an oil or hydrocarbon contaminated site, in combination with microorganism-containing compositions taught herein. In one aspect, a composition can be sprayed directly onto the oil at the site of contamination. Compositions may comprise a microorganism-containing composition comprising Rhodopseudomonas palustris, Bacillus subtilis, Pseudomonas aeruginosa, Saccharomyces cerevisiae, Aspergillus oryzae, Candida utilis, Streptococcus lactis, Lactobacillus caseii Lactobacillus planterum, Lactobacillus helveticus and Lactobacillus caseii. Microorganism-containing compositions may comprise one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition may comprise IN-M1, Accession No. PTA-12383. For example, a microorganism-containing composition may comprise IN-M1, Accession No. PTA-12383 and one or hydrocarbon degrading microorganisms. Methods of using a microorganism-containing composition comprise applying an effective amount of a microorganism-containing composition to a site or container comprising oil or other hydrocarbons and water and/or soil and reducing or eliminating at least a portion of the oil or other hydrocarbons in the water and/or soil.

The present invention comprises compositions and methods useful in treatments for wildlife or other animals that may be affected by pollutants or contaminants. For example, and not to be limiting, the compositions and methods comprise treating birds or other animals or wildlife contaminated by oil or hydrocarbons, thereby reducing the amount of time and handling needed to clean the oil or hydrocarbons from the animals. In one aspect, a microorganism-containing composition may be diluted and grown to provide large quantities of a ready-to use composition in about 5-10 days or a microorganism-containing composition may be used in a concentrated form. Methods of using the compositions disclosed herein in the treatments for animals comprise 1) optionally, diluting the composition, and, spraying a diluted solution onto the coat or feathers of the animal, 2) leaving the compositions on the coat or feathers of the animal for a pre-determined time period such as from minutes to hours, and 3) rinsing the animal or allowing the animal to bathe in a pool of water, or contacting the animal with a composition, comprising an even more diluted concentration of the microorganism-containing composition. This method can be repeated. In one aspect, a shower spray of the compositions can be used to assist the removal of the oil or hydrocarbon residues. Compositions may comprise a microorganism-containing composition comprising *Rhodopseudomonas palustris, Bacillus subtilis, Saccharomyces cerevisiae, Aspergillus oryzae, Candida utilis, Streptococcus lactis, Lactobacillus planterum, Lactobacillus helveticus* and *Lactobacillus caseii*. For example, a variation of a concentrated composition as taught in Example 1 may be used. Microorganism-containing compositions may comprise one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition may comprise IN-M1, Accession No. PTA-12383. For example, a microorganism-containing composition may comprise IN-M1, Accession No. PTA-12383 and one or hydrocarbon degrading microorganisms. Methods of using a microorganism-containing composition comprise applying an effective amount of a microorganism-containing composition to an animal and reducing or eliminating at least a portion of the contaminant, such as oil or other hydrocarbons.

The present invention comprises compositions and methods useful in the bioremediation of soil. In one aspect, the compositions and methods may increase the water retention of the soil. In one aspect, the compositions and methods may stimulate the root growth of plants living on or in the soil. In one aspect, the compositions and methods may reduce the risk of infestation by insects. In one aspect, the compositions and methods may reduce the risk of disease. In one aspect, the compositions may aerate the soil, degrade chemical or organic contaminants, and help the plants to take up the organic nutrients that are naturally present or added in the soil. For example, and not to be limiting, the compositions and methods of the present invention are useful in the elimination of brown patches and areas of dead grass on golf course putting greens. In one aspect, the compositions and methods can reduce the need to irrigate soil in order to maintain healthy plant growth. Compositions can be a concentrate and can either be used as a concentrate, or diluted 100:1 to 1:300 in water, and then can be sprayed on the surface of soil requiring treatment. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. Microorganism-containing compositions may comprise one or more mixed cultures, for example, IN-M1, or compositions comprising IN-LH1, IN-BS1, IN-SC1, and/or IN-RP1, in combination or individually, and/or with other microorganisms. For example, a microorganism-containing composition may comprise IN-M1, Accession No. PTA-12383. For example, a microorganism-containing composition may comprise IN-M1, Accession No. and one or microorganisms, such as microorganisms derived from the treatment site or a similar site. Methods of using a microorganism-containing composition comprise applying an effective amount of a microorganism-containing composition to a site such as all or a portion of a golf course, wherein the retention and maintenance of the grass of the golf course is improved and the transition from chemical and synthetic molecules to sustainable organic maintenance is assisted by such methods.

Bioremediation of soil may also comprise providing a microorganism-containing composition to plants or rhizospheres that may be added to a site or providing a microorganism-containing composition to plants or rhizospheres that are present in a site. For example, at a contaminated or polluted site, plants may be planted in the contaminated or polluted site wherein the plants have had a microorganism-containing composition applied to the roots. A combined composition of a microorganism-containing composition, comprising one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition may comprise IN-M1, Accession No. PTA-12383 combined with organisms derived from the site or a similarly contaminated site may be provided to the plants. The plants are allowed to grow and may be harvested or removed after a certain time period, to remove contaminants from the site without removing the soil itself. The plants may eventually be used as a biomass fuel source. For example, the plants at a contaminated site may be contacted by a microorganism-containing composition, such as one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition may comprise IN-M1, Accession No. PTA-12383 and optionally, the soil may be contacted also. A combined composition of a microorganism-containing composition, such as a microorganism-containing composition comprising one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition may comprise IN-M1, Accession No. PTA-12383 combined with organisms derived from the site or a similar site may be provided to the plants.

Though not wishing to be bound by any particular theory, it is thought that a microorganism-containing composition of the present invention stimulates the formation of a beneficial microfilm on the rhizosphere of plants that allows for interactions between organisms in the soil and the plant. This enhanced interaction allows for better transfer of nutrients into the plants some of which may include metabolites and/or elements derived from the contamination, which results in rapid maturation, flowering, more branching and increased yield of fruiting bodies.

Use of a microorganism-containing composition, such as one or more mixed cultures, for example, IN-M1, or compositions comprising IN-LH1, IN-BS1, IN-SC1, and/or IN-RP1, in combination or individually, and/or with other microorganisms have shown stimulation of plant growth for plants grown in organic material with mychorrhyzal fungi; algae blooms in nutrient solutions were suppressed; suppression of common plant infections; and suppression of algae growth on turf grasses of golf greens and mold on leaves of growing plants.

Compositions and methods of the present invention comprise enhancement of seed germination. Providing a microorganism-containing composition, such as one or more mixed cultures, for example, IN-M1, or compositions comprising IN-LH1, IN-BS1, IN-SC1, and/or IN-RP1, in combination or individually, and/or with other microorganisms to seeds of lettuces and other microgreens showed that seed germination was decreased by 50%. A composition comprising IN-M1 at a concentration of $1 \times 10^6$ cells/mL was sprayed onto lettuce and similar greens seeds. The seeds were germinated hydroponically on an organic matrix and wet weight and shoot height was an average of 20% greater than the same seeds not treated with the composition. Seeds so treated resulted in plants that had a 20% increase in biomass in 7 days, compared to plants in the seeds were not treated.

Seed germination in turf grasses, such as that used in golf courses, was enhanced by treating the turf grass seeds with a microorganism-containing composition, such as one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition comprising IN-M1, Accession No. PTA-12383 at a concentration of $1 \times 10^6$ cells per mL was sprayed on a green where the seed had been scattered on the putting greens of a golf course in the southern US. The Kentucky blue grass was established during the time the summer grass was dormant. The Kentucky Blue grass grew faster, with germination accelerated from 7 days to 5 days and became established at a rate faster than grass where the seeds were not sprayed, in 3 weeks as compared to untreated seeds of 4 weeks.

The present invention comprises compositions and methods useful in the treatment or management of commercial and residential septic systems. Compositions and methods are useful the reduction of sludge from sewers or septic systems, thereby reducing health risks from infections and toxic substances including hydrogen sulfide, ammonia and volatile organic carbons. Compositions and methods are useful in controlling the odors from commercial or residential septic systems. In one aspect, compositions are used to treat biosolids or sludge contained in pipes. In one aspect, methods and compositions can be used to treat biosolids or sludge removed from sewers and lift stations which may be contained at storage facilities. In one aspect, methods and compositions are useful in the remediation of septic seepage or drain fields. In one aspect, compositions and methods can be used to remove fat, oil, and grease (FOG) from wastewater. In one aspect, the compositions and methods can be used to treat water polluted by manure from industrial farms. The compositions can be concentrated (see Example 1) and can either be used as concentrated, or diluted 100:1 to 1:10000 in water, and then can be sprayed on the seepage field or area requiring remediation. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as microorganism-containing compositions may comprise one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition may comprise IN-M1, Accession No. PTA-12383 may be used. Methods of using a microorganism-containing composition comprise applying an effective amount of a microorganism-containing composition to a site or container comprising sludge, allowing the composition to remain for a time period, for example time to grow and reproduce at the treated site or surface, and reducing or eliminating at least a portion of the sludge. Methods of using a microorganism-containing composition comprise applying an effective amount of a microorganism-containing composition to a site or container comprising Fat Oil and Grease (FOG), allowing the composition to remain for a time period, for example time to grow and reproduce at the treated site or surface, and reducing or eliminating at least a portion of the FOG. Methods of using a microorganism-containing composition comprise applying an effective amount of a microorganism-containing composition to holding tank of industrial farm wastes, allowing the composition to remain for a time period, for example time to grow and reproduce at the treated site or surface, and reducing or eliminating at least a portion of the wastes. Compositions may be delivered using existing equipment, and interfacing with existing and new aeration, mixing separation/filtration and, monitoring systems useful in the treatment or management of commercial and residential septic systems.

Applying, as used herein, may be contacting the material with a microorganism-containing composition as taught herein.

The present invention comprises compositions and methods useful in the treatment or management of municipal or industrial wastewater treatment. In one aspect, the compositions and methods can reduce the carbon dioxide, methane, ammonia hydrogen sulfide and other greenhouse gas emissions and odour causing compounds. In one aspect, the compositions and methods may reduce biofilm causing bacteria and ecological upsets like filamentous bacteria in sewer lines, pumping/lift stations and in the waste water treatment plant. In one aspect, the compositions and methods can reduce the biological oxygen demand and chemical oxygen demand in polluted water. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as microorganism-containing compositions, such as one or more mixed cultures, for example, IN-M1, or compositions comprising IN-LH1, IN-BS1, IN-SC1, and/or IN-RP1, in combination or individually, and/or with other microorganisms. For example, a concentrated composition as taught in Example 1 may be used. For example, a microorganism-containing composition may comprise IN-M1, Accession No. PTA-12383 may be used. Methods of using a microorganism-containing composition comprise applying an effective amount of a microorganism-containing composition to a municipal or industrial wastewater system, allowing the composition to remain for a time period, for example time to grow and reproduce at the treated site or surface, and reducing or eliminating at least a portion of the wastes. Compositions may be delivered using existing or new equipment, such as existing and new aeration systems, mixing and monitoring systems and biofilters for municipal or industrial wastewater treatment.

The present invention comprises compositions and methods useful in the treatment and/or recycling of water used in industrial processes. Compositions may comprise a microorganism-containing composition comprising

*Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used.

Methods of using a microorganism-containing composition comprise applying an effective amount of a microorganism-containing composition to a site or container comprising wastes from industrial processes, allowing the composition to remain for a time period, for example time to grow and reproduce at the treated site or surface, allowing the composition to remain for a time period, for example time to grow and reproduce at the treated site or surface, and reducing or eliminating at least a portion of the wastes. For example, compositions and methods are useful in the treatment of animal waste generated at dairy farms in the production of milk. The compositions and methods can reduce the greenhouse gas emissions like carbon dioxide, methane, as well as ammonia and other odor causing compounds in the facility, the lagoons and in the sludge or resulting compost which may be spread on soil as a healthy soil amendment. Compositions and methods may improve the quality and performance of the treated biosolids as a soil amendment. Compositions may be delivered using existing equipment, existing and interfacing with new aeration, mixing and monitoring systems for municipal or industrial wastewater treatment. Compositions may be included in anaerobic and aerobic protocols, interfacing with existing technology and included in together with aeration, mixing and monitoring systems as separate solutions and/or systems industrial waste water recycling.

The present invention comprises compositions and methods useful in the treatment of water contained by dams. In one aspect, compositions and methods are used to treat water contained by a dam for the purposes of generating hydroelectric power. For example, and not to be limiting, the treatment of dammed water can include reducing the output of carbon dioxide from the water source. Compositions may accelerate the degradation of vegetation buried under the water thus reducing greenhouse gas emissions. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container comprising stagnant or contained water, allowing the composition to remain for a time period, for example time to grow and reproduce at the treated site or surface, and reducing or eliminating a portion of the greenhouse gas or carbon dioxide released or present.

The present invention comprises compositions and methods useful in controlling odors generated by composting facilities. The compositions and methods can reduce the carbon dioxide, methane, and other greenhouse gas emissions, as well as reducing ammonia and other odor causing compounds. The compositions and methods may accelerate the composting process in municipal and industrial scale composting facilities. The compositions and methods may decrease heavy metal levels, when present and improve the final product quality and performance as a healthy soil amendment. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container comprising odiferous material and reducing or eliminating at least a portion of the malodors released by the site or container.

The compositions and methods can reduce the corrosive nature of the leachate, render the leachate beneficial to the process and reduce odors thereof. The compositions and methods can interact with biofilter installations augmenting the performance thereof. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*, for example, a concentrated composition as taught in Example 1. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container comprising leachate, allowing the composition to remain for a time period, for example time to grow and reproduce at the treated site or surface, and reducing at least a portion of the corrosive nature of the leachate, rendering at least a portion of the leachate beneficial to the process. The compositions may sequester all or some of the leachate or may alter or modify the leachate to reduce its toxicity.

Compositions of the present invention may be delivered using existing equipment, interfacing with existing and new separated organic waste management facilities including, windrows, static piles and in vessel facilities, anaerobic and aerobic protocols, interfacing with existing equipment and with new equipment or systems for aeration, grinding, mixing, biofilters and monitoring systems as separate solutions and/or systems for municipal or industrial scale composting facilities.

The present invention comprises compositions and methods useful in the decontamination of soil and water that are contaminated as a result of natural disasters. For example, and not to be limiting, a natural disaster can be a flood, an earthquake, a hurricane, a tsunami or any other natural disaster. In one aspect, compositions and methods can be used to suppress at least a portion of the pathogens that enter the water system following a natural disaster. In one aspect, the compositions and methods can be used to remediate water contaminated by *Vibrio cholerae*. The compositions of the present invention can be delivered into the water system requiring remediation by providing a microorganism-containing composition directly to the water, or by use existing equipment or with known delivery systems. Water can be treated in existing locations such as holding tanks, lagoons or directly at the source in latrines, gutters, or stagnant groundwater. Delivery mechanisms can be optimized based on different circumstances. Compositions may comprise a microorganism-containing composition comprising

*Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used. Compositions may comprise natural antibiotic and anti parasitic organisms targeting disease affecting displaced populations and populations plagued by poor sanitation. Methods of using a microorganism-containing composition comprise applying an effective amount of a microorganism-containing composition to a site or container of water comprising unwanted organisms such as *Vibrio cholera*, allowing the composition to remain for a time period, for example time to grow and reproduce at the treated site or surface, and reducing or eliminating at least a portion of the microorganisms such as *Vibrio cholerae*.

The present invention comprises compositions and methods useful in the creation and maintenance of healthy soil environments, thereby allowing for healthy plant growth. Storm or water run-off is treated in engineered reservoirs, or other locations such as on a farm or in an industrial complex, before the run-off water reaches the surface water or contaminates the ground, the run-off is treated with a composition of the present invention. Therefore treating at source before contamination is transported from contaminated site to other sites aids in the creation and maintenance of healthy soil environments. Such treatments may encourage vegetation in the watershed area that will aid in treating the run-off. In one aspect, compositions and methods can be used to ameliorate the contaminating effects of water runoff or storm water runoff by treating at source contamination such as manure pits and golf courses. In one aspect, compositions and methods can be used to ameliorate the contaminating effects of water runoff or storm water runoff by treating porous hard surfaces to clear the pores of the surface to clear organic debris and allow penetration of the storm water through the pores in pervious concrete.

Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container contacted by stormwater runoff, allowing the composition to remain for a time period, for example time to grow and reproduce at the treated site or surface, and reducing or eliminating at least a portion of the contaminants carried to the site or container in the water runoff.

The present invention comprises compositions and methods useful in hydroponic systems for plant growth. Methods of the present invention comprise contacting the root systems of plants grown in hydroponic conditions, or spraying the leaves, stems, fruits or roots of plants grown in a hydroponic system. A dilute concentration, such as $1 \times 10^3$ to $5 \times 10^4$ cells per mL, may be added to the circulating media in a hydroponic system to reduce algae bloom formation and optionally to treat root systems of plants in the circulating media.

Compositions used in such hydroponic systems may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to plants or containers of the plants or providing a composition to the circulating media or other media used in hydroponic growing conditions, allowing the composition to remain for a time period, for example time to grow and reproduce at the treated site or surface, and enhancing the growth of the plants in the hydroponic system, and optionally reducing the amount of algae or other unwanted growth in the media, or on containers or piping.

The present invention comprises compositions and methods useful in the remediation of mold growing in an area following or in damp or humid environments. In one aspect, the compositions and methods can be used to treat and prevent the growth of mold in any building that has sustained water damage as a result of flooding. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, compositions such as microorganism-containing compositions, such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container comprising mold growth and reducing or eliminating at least a portion of the mold growth.

The present invention comprises compositions and methods useful in improving the qualities of soil. In one aspect, compositions and methods may increase the water retention of the soil. In one aspect, compositions and methods may stimulate the root growth of plants living on or in the soil. In one aspect, compositions and methods may reduce the risk of infestation by insects. In one aspect, compositions and methods may reduce the risk of disease. In one aspect, compositions may aerate the soil, degrade chemical or organic contaminants, and help the plants to take up the organic nutrients that are naturally present or added in the soil. Therefore, compositions and methods can be used to enhance the growth of lawns, flowers, fruits, vegetables, orchards or vineyards, trees or forests. In one aspect, compositions and methods can be used in greenhouses. In one aspect, compositions and methods can be used in municipal and urban plantations in difficult environments. In one aspect, compositions and methods can be used at the side of roads where soil is contaminated, for example, with salt and oil. In one aspect, compositions and methods can be used for example, on military facilities where soil may be contaminated with oil, salt, or heavy metals. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container comprising plants, allowing the composition to remain for a time period, for example time to grow and reproduce at the treated site or surface, and enhancing the growth of the plants. Methods of using a microorganism-containing composition comprise applying an effective amount of a microorganism-containing composition to a site or container comprising soil or compost or a mixture thereof, allowing the composition to remain for a time period, for example time to grow and reproduce at the treated site or surface, and improving the soil quality, such as water retention, increased microbial concentration, or other beneficial qualities.

The present invention comprises compositions and methods useful in the control of insects, by the microorganisms of the composition colonizing or being present on the leaf surface and around the plant roots, creating a barrier against harmful insects and fungal spores. The compositions and methods may be used to suppress for example mildew and insect infestations whereby the beneficial microbial species colonize plants and soil. In one aspect, the compositions boost the immune system of the plant to fight infection. In one aspect, compositions of the present invention may act as a delivery system for active agents such as biological insecticides or larvecides as such as bti, as well as natural ingredients. It is theorized that providing a composition of the present invention provides competitive inhibition for pathogenic organisms by the microorganisms in the composition. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as microorganism-containing compositions, such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container comprising plants, allowing the composition to remain for a time period, for example time to grow and reproduce at the treated site or surface, and reducing or eliminating at least a portion of the pathological effects on the plants, or aid in delivery of desired active agents, such as insecticides, larvecides or other desired active agents. Methods of application include, but are not limited to, spraying foliage, soil and fruit.

The present invention comprises compositions and methods useful in bee keeping. In one aspect, the compositions and methods can be used to control *varroa* mites inside bee hives. In one aspect the hives are sprayed inside with a microorganism-containing composition at $5 \times 10^3$ to $5 \times 10^4$ cells per mL in water. In another aspect a microorganism-containing composition can be used to clean and wipe down the hives. It is theorized that providing a composition of the present invention provides competitive inhibition for pathogenic organisms by the beneficial microorganisms in the composition. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as microorganism-containing compositions, such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container comprising insects to remove harmful organisms.

The present invention comprises compositions and methods useful in the techniques of hydroponic or aeroponic agriculture, or in vertical farming methods. Compositions of the present invention can be added to the nutrient solution of the plants to increase the uptake of nutrients by the plants. Compositions may also be sprayed on the plant surfaces and in the air to prevent pathogenic organisms from colonizing leaves and fruiting bodies or growing on the plant Other surfaces and surroundings of plants, including but not limited to containers, shelves, greenhouses, rock wool, growing media surfaces, may be provided compositions of the present invention. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as microorganism-containing compositions, such as one or more mixed cultures, for example, IN-M1, or compositions comprising IN-LH1, IN-BS1, IN-SC1, and/or IN-RP1, in combination or individually, and/or with other microorganisms may be used. Methods may comprise providing a microorganism-containing composition to all or a portion of a plant or seeds, allowing the composition to remain for a time period, for example time to grow and reproduce at the treated site or surface, and enhancing the biological activities of the plant or seeds, such as increasing germination rate, increasing biomass of the plant, reducing or modulating infection of the plant or seeds, increasing fruit setting rate and flowering, increasing tuber development, increasing the length of production time for the plants, increasing the productive lifespan of the treated plant, increasing nutrient uptake, and treating the plants and seeds, and fluids or surfaces contacted by the plant or seeds, such as media or containers, to reduce a portion of the pathogenic or endogenous microbes present.

The present invention comprises compositions and methods useful in aquaculture or pisciculture. In one aspect a microorganism-containing composition is used to suppress odors. In another aspect a microorganism-containing composition is used to degrade fish waste, ammonia and suppresses algae. In another aspect a microorganism-containing composition suppresses infection and is beneficial for fish coats and digestion. Compositions may comprise a microorganism-containing composition comprising *Rhodopseudomonas palustris, Bacillus subtilis, Pseudomonas aeruginosa, Sac-*

*charomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container comprising fish or fish wastes, or waters in which fish are kept, allowing the composition to remain for a time period, for example time to grow and reproduce at the treated site or surface, and reducing the odors or unwanted algal growth, or aiding in the growth of the fish.

The present invention comprises compositions and methods useful in the decontamination of industrial by-products from and used in the construction industry. In one aspect, a microorganism-containing composition of the present invention can be used as an additive to concrete or added to cement during the cement-making process to increase permeability.

The present invention comprises compositions and methods useful in the healthcare industry. For example, and not to be limiting, the compositions and methods can be used to enhance air quality, suppress pathogens, clean and sanitize healthcare facilities or remediate toxic waste generated by healthcare facilities. Additionally, compositions of the present invention may be to aid in human or animal health. For example, the compositions may be used as source material for the extraction or purification of active agents that are useful as food supplements, in cosmetics or are nutriceutical cosmeceticals, probiotic or pharmaceutical compositions such as antioxidants and biological substances and compounds that aid digestive processes and gastrointestinal disease. Compositions may be added to foods or cosmetics, or may function as supplements separately from foods. Compositions may comprise factors isolated from or a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* and/or *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container, allowing the composition to remain for a time period, for example time to grow and reproduce at the treated site or surface, and at least a portion of the pathogenic organisms are reduced or eliminated. A composition of the present invention may provide competitive inhibition by colonizing a surface and preventing the colonization of pathogenic bacteria, such as MRSA. Compositions of the present invention may be used in treatment methods of biological, chemotoxic (including urine and other biological waste from cancer patients and other patients) and radioactive waste including radioactive isotope tracers, treatments and implant patients at source, and comprise providing a microorganism-containing composition to a site to be treated, allowing the composition to remain for a time period, for example time to grow and reproduce at the treated site or surface, and reducing or eliminating at least a portion of the waste or unwanted materials or pathogens.

The present invention comprises compositions and methods useful in the transportation industry. For example, and not to be limiting, the compositions and methods can be used to clean or treat diesel spills form engines trucks, trains or aircraft. In one aspect, microorganism-containing compositions and methods can be used to treat wastewater generated on passenger buses, trains or aircraft. Compositions of the present invention may be used in treatment methods for wastes from latrines, portapotties, oily water, such as bilge water, waste water from toilet facilities, restaurant and kitchens on transportation vehicles, vessels and the like. For example, compositions such as one or more mixed cultures, for example, IN-M1, or compositions comprising IN-LH1, IN-BS1, IN-SC1, and/or IN-RP1, in combination or individually, and/or with other microorganisms may be used.

The present invention comprises compositions and methods useful in the raising or keeping of animals. For example, and not to be limiting, the animals can be raised or kept as pets or as farm animals and can be dogs, cats, horses, cows, pigs or fish. In one aspect, the compositions and methods can be used to control animal odor. In one aspect, this can be accomplished by spraying the compositions on the animal's bedding or directly on the animal. In one aspect, animals can ingest the compositions of the present invention with their food or water, thereby improving their health, digestion and odor. Compositions may comprise a microorganism-containing composition comprising *Rhodopseudomonas palustris, Bacillus subtilis, Pseudomonas aeruginosa Saccharomyces cerevisiae, Aspergillus oryzae, Candida utilis, Streptococcus lactis, Lactobacillus planterum, Lactobacillus helveticus* and *Lactobacillus caseii*. For example, a concentrated composition as taught in Example 1 may be used. For example, compositions such as one or more mixed cultures, for example, IN-M1, or compositions comprising IN-LH1, IN-BS1, IN-SC1, and/or IN-RP1, in combination or individually, and/or with other microorganisms may be used. Methods of using a microorganism-containing composition comprise applying an effective amount of a microorganism-containing composition to a site or container which is contacted by an animal and reducing or eliminating at least a portion of the odors, or the pathogenic organisms. Methods may comprise providing a microorganism-containing composition as an animal feed.

The present invention comprises compositions useful as additives in products for human consumption or use. For example, and not to be limiting, the compositions can be used as additives in probiotic health drinks and food supplements alcoholic or non-alcoholic fermented beverages, fermented foods, salad dressings, marinades, culinary spices or supplements, dietary supplements, shampoos, soaps, anti-fungal medications, toothpaste or mouthwash. Compositions may comprise a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* or *Lactobacillus caseii*, in combination, or individually. For example, a concentrated composition as taught in Example 1 may be used. For example, compositions such as microorganism-containing compositions, such as one or more mixed cultures, for example, IN-M1, or compositions comprising IN-LH1, IN-BS1, IN-SC1, and/or IN-RP1, or a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* or *Lactobacillus caseii*, in combination or individually, and/or with other microorganisms may be used.

Methods of using a microorganism-containing composition comprise adding an effective amount of a microorganism-containing composition to a foodstuff, cosmetic agent, cleansing agent or providing a composition as an ingestible composition. Foodgrade products may be fermented with the microorganisms.

The present invention comprises compositions that can be ingested or applied as medications. For example, and not to be limiting, microorganism-containing compositions can be used as treatment compositions for skin or hair disorders, or digestive ailments. For example, compositions such as one or more mixed cultures, for example, IN-M1, or compositions comprising IN-LH1, IN-BS1, IN-SC1, and/or IN-RP1, or a microorganism-containing composition comprising *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* or *Lactobacillus caseii*, in combination or individually, and/or with other microorganisms may be used.

The present invention comprises compositions and methods useful in domestic settings such as a household.

Methods and compositions disclosed herein may comprise use of microorganisms that are from treatment sites, such as biological surfaces of plants or animals, or environmental sites such as contaminated or polluted sites, and such microorganisms are added to or admixed with a microorganism-containing composition of the present invention. Methods comprise adding microorganisms isolated from a treatment site to compositions comprising one or more mixed cultures, for example, IN-M1, or compositions comprising IN-LH1, IN-BS1, IN-SC1, and/or IN-RP1, or *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* or *Lactobacillus caseii*, in combination or individually, and/or with other microorganisms to form combined compositions. Such combined compositions may be used at the originating sites to remove contaminants, or other desired treatments. This is sometimes referred to as in situ remediation, which utilizes the indigenous, contaminant-degrading microorganisms which are present at the contaminated site. These organisms are present at the site and are capable of some kind of degradation of an element of the site. Generally, when unaltered and in its original state, the indigenous microorganisms' decontaminating action proceeds at too low a level and too slow a rate to effectively decontaminate the area. Additionally, the organisms may be only able to chemically change one contaminant in a mixed collection of pollutants, or only make a few chemical changes in a chemically-complex contaminating molecule. The growth and activities of the naturally occurring microorganisms are enhanced by forming a combined composition comprising a microorganism-containing composition of the present invention. A method for making a combined composition comprises feeding and growing a small amount of organisms from the contaminated soil or water site and admixing it with a microorganism-containing composition to stimulate growth of a natural beneficial microbial remediation community or microorganisms. This combined composition of the present invention culture may be then reintroduced into the contaminated environment or used in other similar situations. For example, compositions such as one or more mixed cultures, for example, IN-M1, or compositions comprising IN-LH1, IN-BS1, IN-SC1, and/or IN-RP1, or *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus* or *Lactobacillus caseii*, in combination or individually, and/or with other microorganisms may be combined with organisms from a polluted or contaminated site, and the combined composition may be grown in a container or may be added to the contaminated or polluted site, or sites similar to the original site to modulate, such as enhance, the breakdown occurring at the site.

It will be understood that the aspects of the present invention which have been described are illustrative of some of the applications of the principles of the present invention. Numerous modifications may be made by those skilled in the art without departing from the true spirit and scope of the invention.

The terminology used herein is for the purpose of describing particular aspects only and is not intended to be limiting.

As used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

The word "or" as used herein means any one member of a particular list and also includes any combination of members of that list.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "treating" refers to inhibiting, preventing, curing, reversing, attenuating, alleviating, minimizing, suppressing or halting the deleterious effects of a condition, contaminant, toxicant, pollutant and/or causing the reduction, remission, or regression of a condition. Those of skill in the art will under-stand that various methodologies and assays can be used to assess the development of a condition, and similarly, various methodologies and assays may be used to assess the reduction, remission or regression of the condition.

As used herein, the term "determining" can refer to measuring or ascertaining a quantity or an amount or a change in activity. For example, determining the characteristics of microorganisms or growing cultures as used herein can refer to the steps that the skilled person would take to measure or ascertain some quantifiable value in a sample. The art is familiar with the ways to measure characteristics in a sample. The term sample is used in its common meaning of a portion from a larger solution, from a site, from a culture, or other larger entity from which a portion, the sample, can be removed and optionally acted upon.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

The present invention comprises microorganism-containing compositions and methods for making and using such compositions. For example, a microorganism-containing composition comprises a composition comprising isolated bacteria, at least one isolated yeast, and at least one isolated micorrhyzal fungus, wherein the bacteria comprise at least a *lactobacillus*, and at least a *bacillus*, wherein the bacteria were selected based on enzyme profiles so that the bacteria are complementary. The *Lactobacillus* may be *L. helveticus*, or the *Lactobacillus* may be *L. helveticus*, IN-LH1, Accession No. PTA-12386. The *Bacillus* may be *B. subtilis*, or the *Bacillus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus*, and *Lactobacillus casei*, or a microorganism-containing composition may comprise one or more of the microorganisms disclosed herein.

A method using a composition of the present invention comprises a method of bioremediation of a site, comprising, providing a microorganism-containing composition to a site comprising at least one contaminant, wherein the microorganism-containing composition comprises at least one isolated bacteria, at least one isolated yeast, and at least one isolated micorrhyzal fungus, wherein the bacteria comprise at least a *lactobacillus* and at least a *bacillus*, wherein the bacteria were selected based on enzyme profiles so that the bacteria are complementary, allowing the microorganisms of the microorganism-containing composition to grow and reproduce for a period of time; and reducing at least a portion of at least one contaminant at the site. The *Lactobacillus* may be *L. helveticus*, or the *Lactobacillus* may be *L. helveticus*, IN-LH1, Accession No. PTA-12386. The *Bacillus* may be *B. subtilis*, or the *Bacillus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus*, and *Lactobacillus casei*, or a microorganism-containing composition may comprise one or more of the microorganisms disclosed herein. The method may further comprise, at a predetermined time after providing the microorganism-containing composition, measuring the level or amount of at least one contaminant at the site and comparing it to a measurement of the level or amount of at least one contaminant at the site obtained prior to providing the microorganism-containing composition. The method may further comprise at a predetermined time after providing the microorganism-containing composition, assessing at least one characteristic of the condition of the contaminated site and comparing it to that characteristic of the condition of the site prior to providing the microorganism-containing composition. Assessing at least one characteristic of the condition of the site may comprise measuring at least one characteristic of the site, wherein a characteristic comprises the color, the smell, the cleanliness, the amount of plant growth, the amount of microbial growth, the amount of animal growth, the amount of biosolids, at the site and comparing that characteristic measurement to a measurement of that characteristic of the condition of the site taken prior to providing the microorganism-containing composition, to provide a measurement of a change in the condition of the site. The site may comprise a mine, a municipal water system, a contaminated site, a polluted site, a septic system, a golf course, lentic water, a lake, a pond, a contained body of water, lotic water, a flowing stream, a moving body of water, a circulating contained body of water, leachate from a landfill, a mine tailing, industrial waste water or soil, a contained body of soil, contained material removed from a contaminated site, water or soil behind a dam, water or soil from a farm or facility with animals, water or soil from a farm or a facility for plants, water or soil from a waste treatment plant, such as a landfill, municipal water and waste treatment system, commercial water and waste treatment system, industrial water and waste treatment system, or private water and waste treatment system. The method may further comprise, prior to adding the microorganism-containing composition to the site, obtaining a sample from the site and adding at least a portion of the sample to the microorganism-containing composition to form a combined microorganism-containing composition, and allowing microorganisms of the combined microorganism-containing composition to grow and reproduce. The method may further comprise providing the combined microorganism-containing composition comprising one or more microorganisms from the site to the site.

A method using a composition of the present invention comprises a method of affecting, enhancing, modulating, stimulating or aiding plant growth, comprising, providing a microorganism-containing composition to a site where plants are grown, to a plant or to a plant at a particular growth stage, or combinations thereof, wherein the microorganism-containing comprises at least one isolated bacteria, at least one isolated yeast, and at least one isolated micorrhyzal fungus, wherein the bacteria comprise at least a *lactobacillus* and at least a *bacillus*, wherein the bacteria were selected based on enzyme profiles so that the bacteria are complementary; and allowing microorganisms of the microorganism-containing composition to grow and reproduce for a period of time. The *Lactobacillus* may be *L. helveticus*, or the *Lactobacillus* may be *L. helveticus*, IN-LH1, Accession No. PTA-12386. The *Bacillus* may be *B. subtilis*, or the *Bacillus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus*, and *Lactobacillus casei*, or a microorganism-containing composition may comprise one or more of the microorganisms disclosed herein. The method may comprise applying the microorganism-containing composition to the seeds of plants. The method may comprise applying the microorganism-containing composition to the roots of plants. The method may comprise applying the microorganism-containing composition to the leaves and stalks of plants. The method may comprise enhancing seed germination. The method may comprise enhancing root production. The method may comprise increasing the per plant yield of treated plants compared to untreated plants. The method may comprise increasing the biomass of the treated plants compared to untreated plants. The method may comprise increasing the fruit production of the treated plants compared to untreated plants. The method may comprise increasing the production period of the treated plants compared to untreated plants. The method may comprise increasing the productive lifespan of the treated plants compared to untreated plants. The method may comprise using the method with plants grown under hydroponic conditions. The method may comprise using the method with plants grown in a greenhouse. The method may comprise using the method with plants grown in a field or outside. The method may comprise using the method with plants grown in aeroponic conditions, or combined hydroponic and aeroponic conditions. The method may comprise using the method with vertical farming.

A method using a composition of the present invention comprises a method of treating a surface comprising providing a microorganism-containing composition to a surface, wherein the microorganism-containing composition comprises at least one isolated bacteria, at least one isolated yeast, and at least one isolated micorrhyzal fungus, wherein the bacteria comprise at least a *lactobacillus* and at least a *bacillus*, wherein the bacteria were selected based on enzyme profiles so that the bacteria are complementary; and allowing microorganisms of the microorganism-containing composition to grow and reproduce for a period of time, wherein the microorganisms compete with endogenous bacteria (whether originally present or added over time from the environment) for at least one environmental factors comprising physical space, nutrients, water, oxygen, or light or chemical energy sources, or combinations thereof, or wherein the microorganisms of the microorganism-containing composition predate and remove microorganisms originally present on the surface. The method may comprise lowering the number of originally present microorganisms. The *Lactobacillus* may be *L. helveticus*, or the *Lactobacillus* may be *L. helveticus*, IN-LH1, Accession No. PTA-12386. The *Bacillus* may be *B. subtilis*, or the *Bacillus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus*, and *Lactobacillus casei*, or a microorganism-containing composition may comprise one or more of the microorganisms disclosed herein.

A method using a composition of the present invention comprises treating a fluid, comprising, providing a microorganism-containing composition to a fluid, wherein the microorganism-containing composition comprises at least one isolated bacteria, at least one isolated yeast, and at least one isolated micorrhyzal fungus, wherein the bacteria comprise at least a *lactobacillus* and at least a *bacillus*, wherein the bacteria were selected based on enzyme profiles so that the bacteria are complementary; and allowing microorganisms of the microorganism-containing composition to grow and reproduce for a period of time, wherein the microorganisms compete with endogenous bacteria (whether originally present or added over time from the environment) for at least one environmental factors comprising physical space, nutrients, water, oxygen, or light or chemical energy sources, or combinations thereof, or wherein the microorganisms of the microorganism-containing composition predate and remove microorganisms originally present in the fluid. The method may comprise lowering the number of coliforms in the liquid. The *Lactobacillus* may be *L. helveticus*, or the *Lactobacillus* may be *L. helveticus*, IN-LH1, Accession No. PTA-12386. The *Bacillus* may be *B. subtilis*, or the *Bacillus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus*

*planterum, Lactobacillus helveticus*, and *Lactobacillus casei*, or a microorganism-containing composition may comprise one or more of the microorganisms disclosed herein.

A method using a composition of the present invention comprises making an article comprising a microorganism-containing composition, comprising, adding a microorganism-containing composition to a surface of an article, wherein the microorganism-containing composition comprises at least one isolated bacteria, at least one isolated yeast, and at least one isolated micorrhyzal fungus, wherein the bacteria comprise at least a *lactobacillus* and at least a *bacillus*, wherein the bacteria were selected based on enzyme profiles so that the bacteria are complementary. The method may comprise steps where the microorganism-containing composition and surface are dried to attach the microorganism-containing composition to the surface. The method may comprise steps where the surface is treated to aid in attachment of the microorganism-containing composition. The method may comprise adding one or more components to the microorganism-containing composition to aid in its attachment to the surface. The method may comprise adding one or more components to both the microorganism-containing composition and the surface to aid in attachment of the microorganism-containing composition to the surface. Such components may be any material, compound or molecule that aids in the attachment of the microorganism-containing composition to the surface or the article. For example, glues, starches, natural materials, polymeric materials and materials that are known for attaching microorganisms to surfaces or articles. The method may comprise surfaces or articles wherein the surface or article is is a glass bead, inert materials, woven materials, nonwoven materials, natural materials such as plant material, coco mats, silica beads, polymeric materials, plant container, container, filter structures, porous inert particles, or zeolites. Articles made with attached microorganism-containing compositions of the present invention are contemplated by the invention. The *Lactobacillus* may be *L. helveticus*, or the *Lactobacillus* may be *L. helveticus*, IN-LH1, Accession No. PTA-12386. The *Bacillus* may be *B. subtilis*, or the *Bacillus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus*, and *Lactobacillus casei*, or a microorganism-containing composition may comprise one or more of the microorganisms disclosed herein.

A method using a composition of the present invention comprises a method for making a food supplement, comprising, growing a microorganism-containing composition to a particular cellular concentration, wherein the microorganism-containing composition comprises at least one isolated bacteria, at least one isolated yeast, and at least one isolated micorrhyzal fungus, wherein the bacteria comprise at least a *lactobacillus* and at least a *bacillus*, wherein the bacteria were selected based on enzyme profiles so that the bacteria are complementary, and isolating factors from the microorganisms or the media. Factors made by microorganisms that useful as food supplements are known and methods for isolating them are known to those skilled in the art. The *Lactobacillus* may be *L. helveticus*, or the *Lactobacillus* may be *L. helveticus*, IN-LH1, Accession No. PTA-12386. The *Bacillus* may be *B. subtilis*, or the *Bacillus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus*, and *Lactobacillus casei*, or a microorganism-containing composition may comprise one or more of the microorganisms disclosed herein.

A method using a composition of the present invention comprises a method for making a food supplement, comprising growing a microorganism-containing composition to a particular cellular concentration, wherein the microorganism-containing composition comprises at least one isolated bacteria, at least one isolated yeast, and at least one isolated micorrhyzal fungus, wherein the bacteria comprise at least a *lactobacillus* and at least a *bacillus*, wherein the bacteria were selected based on enzyme profiles so that the bacteria are complementary, and drying and packaging the composition for use as a food supplement. Food supplements comprising microorganisms are known and methods for preparing and packaging them are known to those skilled in the art. The *Lactobacillus* may be *L. helveticus*, or the *Lactobacillus* may be *L. helveticus*, IN-LH1, Accession No. PTA-12386. The *Bacillus* may be *B. subtilis*, or the *Bacillus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus*, and *Lactobacillus casei*, or a microorganism-containing composition may comprise one or more of the microorganisms disclosed herein.

A method using a composition of the present invention comprises a method for food supplementation, comprising adding to animal, plant or human food, a microorganism-containing composition comprising, isolated bacteria, at least one isolated yeast, and at least one isolated micorrhyzal fungus, wherein the bacteria comprise at least one of a *lactobacillus*, and at least one of a *bacillus*, wherein the bacteria were selected based on enzyme profiles so that the bacteria are complementary. The *Lactobacillus* may be *L. helveticus*, or the *Lactobacillus* may be *L. helveticus*, IN-LH1, Accession No. PTA-12386. The *Bacillus* may be *B. subtilis*, or the *Bacil-

*lus* may be *B. subtilis*, IN-BS1, Accession No. PTA-12385. The yeast may be *Saccharomyces cerevisiae*, or the yeast may be *Saccharomyces cerevisiae*, referred to as IN-SC1, Accession No. PTA-12384. The microorganism-containing composition may further comprise an isolated photosynthetic bacteria. The photosynthetic bacteria may be *Rhodopseudomonas palustris*, or the photosynthetic bacteria is *Rhodopseudomonas palustris*, IN-RP1, Accession No, PTA-12387. The microorganism-containing composition comprises a mixed culture of isolated microorganisms. A mixed culture may be IN-M1, Accession No PTA-12383. A mixed culture may comprise *Rhodopseudomonas palustris, Bacillus subtilis, Pseudomonas aeruginosa, Saccharomyces cerevisiae, Aspergillus oryzae, Candida utilis, Streptococcus lactis, Lactobacillus planterum, Lactobacillus helveticus,* and *Lactobacillus casei*, or a microorganism-containing composition may comprise one or more of the microorganisms disclosed herein.

A method of the present invention comprises a method for making a mixed culture, comprising, measuring one or more enzyme activities of a plurality of types or species of microorganisms to form an enzyme profile for each microorganism, wherein an enzyme profile comprises one or more enzymes and the level of activity for the one or more enzymes for a particular substrate; selecting two or more microorganisms of a) wherein the enzyme profile of each selected microorganism is not identical to the enzyme profile of another microorganism so that at least one enzyme and/or at least one enzyme activity of the enzymes of the profile is found in only one microorganism in the mixed culture, growing the selected microorganisms in media to form an incubation mixture. The method may comprise measuring characteristics of the incubation mixture. Measuring characteristics of the incubation mixture may comprise measuring the predation of one or more selected microorganism by one or more other selected microorganisms, measuring factors or proteins released or made by one or more microorganisms, pH changes, or extracellular enzymes excreted by one or more selected microorganisms and its effects on one or more other selected microorganism, measuring the number of cells per mL of one or more selected microorganism in the mixture, determining growth rate for one or more selected microorganisms, or combinations of characteristics and measurements. The method may comprise using the measured characteristics of the incubation mixture to determine if one or more microorganisms are to be removed from the incubation mixture or if one or more microorganisms are to be added to the incubation mixture. The method may comprise wherein when one or more microorganisms are to be removed from the incubation mixture, the method may comprises killing the incubation mixture and repeating the steps to make a new incubation mixture without the identified unwanted microorganism. The method may comprise steps wherein when one or more microorganisms are to be added to the incubation mixture, the method may comprise adding one or more desired isolated microorganisms to the incubation mixture, and growing the mixture to a predetermined cellular concentration to produce a mixed culture, and optionally, packaging all or a portion of the mixed culture. The method may comprise repeating the steps of the method one or more times. The method may comprise growing the cells of the incubation mixture to a particular concentration to form an individual mixed culture. The method may comprise making one or more mixed cultures and f) combining the individual mixed cultures to form a mixed culture. The method may comprise growing the mixed culture to a particular concentration; and packaging all or portions of the mixed culture. The method may comprise growing the mixed culture to form an incubation mixed culture and measuring characteristics of the incubation mixed culture. The method may comprise steps of measuring characteristics of the incubation mixed culture comprises measuring the predation of one or more selected microorganism by one or more other selected microorganisms, measuring factors, pH changes, or extracellular enzymes excreted by one or more selected microorganisms and its effects on one or more other selected microorganism, measuring the number of cells per mL of one or more selected microorganism in the mixture, determine growth rate for one or more selected microorganisms, or combinations of measurements. The method may comprise using the measured characteristics of the incubation mixed culture to determine if one or more microorganisms is to be removed from the incubation mixed culture or if one or more microorganisms is to be added to the incubation mixed culture, or if no change in microorganisms is to be made. The method may comprise steps for when one or more microorganisms are to be removed from the incubation mixed culture, the method further comprises killing the incubation mixed culture; and repeating the steps to make a new incubation mixture without the undesired one or more microorganisms. The method may comprise repeating steps of the method one or more times. The method may comprise steps wherein when one or more microorganisms are to added to the incubation mixed culture, the method further adding one or more isolated microorganisms to the incubation mixed culture, and growing the incubation mixed culture to a predetermined cellular concentration to produce a mixed culture, and optionally, packaging all or a portion of the mixed culture.

EXAMPLES

Example 1

A Method for Making a Microbial Composition

A microorganism, such as a bacteria or yeast, was selected for inclusion in the composition, based on its enzyme activity profile, its ability to grow in media, its lack of spore formation, or other criteria described herein. The microorganism was grown in standard medium for that organism and when at an exponential growth phase, was aliquoted and stored. The media for growing microorganisms, such as yeasts and bacteria, are known to those skilled in the art.

For example, in making I-M Lab, an aliquot (5 mL of cells at $1 \times 10^6$) of each of IN-LH1, IN-BS1 and *l. casei* were added to a media suitable for lactobacilli and *bacillus*, such as Water 700 ml, Molasses 37.5 g, bentonite clay, 3.75 g, Sea salt 3.75 g, Water 720 ml. The bacteria were grown to an OD 0.752.

In making I-M PNSB, an aliquot (5 mL of cells at $1 \times 10^6$) of IN-RP1 was added to a media suitable for phototrophic bacteria. For example Water 134 ml, Fish emulsion 9 ml, IN-SC1 culture ($1 \times 10^6$) 1 ml, volume was adjusted to 144 ml with water and the cells were grown to an OD 0.856.

In making I-M Yeast, an aliquot (5 mL of cells at $1 \times 10^6$) of IN-SC1 and *A. oryzae* (OD 0.3) South River Miso Company, in Conway, Mass., USA were added to a media suitable for yeast, such as Water 390 ml, Molasses 1 g, Fish emulsion 29 g, Kelp 9 g, Wheat germ 1 g.

The volume was adjusted to 432 ml with water. Fish emulsion (a commercially available organic soil amendment, from Nutrivert, Dunham, Quebec non-pasteurized), and the bacteria were grown to an OD 0.574.

To make a compositions such as microorganism-containing compositions, such as IN-M1 deposited with ATCC Accession No. PTA-12383, a mixed culture, the three microbial component mixed cultures were used. I-M Lab, I-M PNSB and I-M Yeast were added to a medium comprising water, molasses, mineral powder, sea salt and wheat bran as shown below. The three microbial component mixtures were added in the percentages shown in the chart below. The seed culture (an initial mixed culture) comprised IN-RP1, IN-BS1, IN-SC1, *Aspergillus oryzae*, IN-LH1, and *Lactobacillus caseii* and was made under sterile conditions.

| Components of Composition | % |
|---|---|
| WATER | 88.70 |
| MOLASSES | 5.00 |
| I-M LAB | 2.00 |
| I-M PNSB | 2.00 |
| I-M YEAST | 1.00 |
| Bentonite clay (Utah) | 0.10 |
| SEA SALT (commercially available) | 0.10 |
| WHEAT BRAN | 0.10 |
| TOTAL | 100 |

The molasses, sea salt, wheat bran and mineral powder were dissolved in some of the warm water and the temperature was kept at 45-50° C. The I-M LAB, the I-M PNSB and I-M Yeast were added together into a separate container and blended. The total was 50 L, of which 20 L was I-M LAB, 20 L was I-M PNSB, and 10 L was I-M Yeast (the composition comprising these three microbial compositions may be referred to herein as a seed culture). This seed culture was added to the main tank of media and water was added to make 110 L, and the temperature was kept at 37° C. with light agitation until the pH is pH 4.0 and below.

A secondary fermentation culture (a mixed culture) was made to produce a stable concentrated culture (mixed culture) comprising approx. 1 billion microorganisms per liter ($1 \times 10^6$ cells/mL). A concentrated composition may have a shelf life of 3 years or more. A typical 1000 liter secondary fermentation batch, was inoculated with 50 liters of the seed culture (described above—20 L was I-M LAB, 20 L was I-M PNSB, and 10 L was I-M Yeast) and the media was 50-200 liters of non-sulphur agricultural molasses, 3.75 liters wheat bran, (0.02-0.05% by volume), 3.75 liters kelp, (0.02-0.05% by volume), 3.75 liters bentonite clay, (0.02-0.05% by volume), 1.25 liters fish emulsion (a commercially available organic soil amendment, from Nutrivert, Dunham, Quebec non-pasteurized, 1.25 liters soy flour, (0.005-0.03% by volume), 675 mg commercially available sea salt, and enough non-chlorinated warm water to make 1000 L.

The pH dropped to about 3.7 by Day 5 after inoculation, and the culture was grown and stirred lightly once per day and pH was monitored. The culture was incubated for 6 weeks, resulting in the microorganism-containing composition used in the following examples. The composition was bottled and stored under anoxic conditions in airtight containers out of sunlight at room temperature. This resulting composition may be referred to as a concentrated composition, with cells at $1 \times 10^6$ cells/mL.

In an alternative method, the secondary fermentation may contain one or more strains of microorganisms, such as those purchased from commercial entities, and/or endogenous microorganisms or microbial consortia isolated from an environment to be treated or a site to be remediated, or a similar environment or site, and may include one or more pollutant(s) or contaminants found in a polluted or contaminated site. By similar site, it is meant that the similar site has the same contaminants, or contaminants that are chemically or physically similar to ones found in the site to be treated, remediated or to which it is desired to apply or provide a composition of the present invention.

Example 2

Use of the Compositions and Methods to Control and Reduce Pond Sludge

On day 1, a 50 liter ($5 \times 10^6$ cells per ml) a composition of the present invention, which was the result of inducing growth in a closed container of 80 Liters water plus 10 liters of molasses and an aliquot of 10 Ls of the concentrated composition of Example 1, was poured into the pond at a dilution of approximately 100:1-1:10000 and was circulated and aerated via a pump for three hours per day. On day 14, a second 50 liters of the composition above was added to the pond and the body of water was circulated and aerated as before. On day 25, the duck weed began to die off and could be removed from the surface of the pond into the gully with a hose. Odor from the sediment also disappeared. On day 30, the pond was clear of algae and duck weed. Past day 30, the remediation process continued to improve water chemistry, lowering phosphate and nitrogen levels. Furthermore, the water clarity improved, there were no odors present, and the organic sludge continued to float to the surface of the pond as it was digested by the microorganisms and could be removed easily.

Example 3

Use of Microorganism-Containing Composition and Methods to Control Odor Caused by Shallow Pond Sludge Two shallow interconnecting ponds were inoculated with the concentrated composition of Example 1. In the upper pond, concentrated secondary fermentation product was diluted 1:100 in water and 15 liters were sprayed on the surface and edges of the pond. No aeration was used. In the lower pond, 10 liters was sprayed on the pond surface and edges of the pond, and, again, no aeration was used. In the adjacent septic seepage field, 5 liters of the concentrated composition of Example 1 was sprayed on the ground and grass in and surrounding the field. Within one hour, odors subsided and continued to be controlled. Further spraying of the seepage field was done as needed, and, during the following weeks, the water in the ponds clarified.

Example 4

Use of the Compositions and Methods to Control Odor Caused by Pond Sludge

A concentrated ($1 \times 10^6$ cells/mL) secondary fermentation composition of Example 1, was diluted 1:100 in water and 30 liters were sprayed on the surface and edges of the pond. No aeration was used. On day 14, 30 liters of pond water from the pond to be treated was blended with 30 ml concentrated secondary fermentation composition of Example 1 incubated at ambient temperature for 5 days and then sprayed on the pond surface and edges of the pond. No aeration was used. Within 3 hours of the initial inoculation odors subsided and continued to be controlled. The control of odor and improvement in water clarity continued throughout the summer and autumn following the treatment.

Example 5

Use of the Compositions and Methods to Remediate Soil

A variation of a concentrated ($1\times10^6$ cells/mL) composition of Example 1, where no *pseudomonas* was included in the original composition, was diluted 1:100 in water, and 5 gallons per acre was sprayed onto the tee boxes, greens, and fairways of a golf course. Sensitive areas such as tees and greens, as well as hot spots or brown spots, were sprayed once or twice per week with the concentrated secondary fermentation product or a variation of the microorganism-containing composition that was diluted 1:100 in water. Seven days after the application of the product, brown spots on putting greens were no longer visible.

Example 6

Use of the Compositions and Methods in the Raising of Animals

Dogs were given the concentrated ($1\times10^6$ cells/mL) composition of Example 1 as an additive in their food, twice daily, at a dose of 1% by weight of the food. The administration of the concentrated composition of Example 1 led to improvement in body odor, reduced flatulence, whitening of the teeth, and reduced symptoms of gingivitis, including a reduction of tarter as well as redness of the gums. The dogs were also given the concentrated composition of Example 1 externally as a shower/rinse once per week at a dose of 3% by volume. The use of the concentrated composition of Example 1 led to improved skin condition and the control of bad odors from the animal's coat.

Cats were given the concentrated ($1\times10^6$ cells/mL) composition of Example 1 as an additive in their food, twice daily, at a dose of 1% of the food by weight. The administration of the concentrated composition of Example 1 improved bad breath, and resulted in a softer and shinier coat.

Indoor farm animal enclosures such as barns, stalls, litter wood shavings, and wood pellets were sprayed with the concentrated composition of Example 1, at a concentration of 3% by volume. During the first week of treatment, the enclosures were sprayed with the concentrated composition of Example 1 twice daily. During the second week of treatment, the enclosures were sprayed with the product once daily. Thereafter, the enclosures were sprayed with the concentrated composition of Example 1 on a weekly basis. Use of the concentrated composition of Example 1 resulted in a reduction of odors in the enclosures and facilitated in the cleaning of stalls and other environments.

Horses were given 50 cc of the concentrated ($1\times10^6$ cells/mL) composition of Example 1 daily, at a dose of 3% dilution by weight in beet pulp. Use of the concentrated composition of Example 1 resulted in improved coats, which became shinier within 3 to 7 days. Furthermore, urine became clearer within 2 weeks of use, and manure degraded faster. Additionally, the horses were given the composition of Example 1 externally as a shower/rinse at a dose of 3% by volume. External use kept black house flies away from the horses, and horses that were nervous of being sprayed with standard or natural insecticides showed no reaction to the use of the product.

A parrot was given the concentrated ($1\times10^6$ cells/mL) composition of Example 1 externally as a spray at a dose of 1% dilution by volume. No adverse effects were observed from preening after administration of the concentrated composition of Example 1. The concentrated composition of Example 1 was also used to spray the parrot's cage. Use of the composition of Example 1 resulted in a reduction of odors and dust from the cage.

Example 7

Use of the Compositions and Methods to Treat and Maintain a Residential Septic System A family with a residential septic system, having a flow rate of 1200 liters per day, began to experience problems with odors backing up into the residence and outside of the residence as the effluent was pumped into the seepage field. Upon inspection, it was noted that a 30 cm crust of bio-solids was floating on the top of the drop out tank, and there were blockages in the in-flow and out-flow pipes. 250 ml of the concentrated ($1\times10^6$ cells/mL) composition of Example 1 was added after breaking through the floating crust. Additionally, a simple aeration device was put into the drop out tank. An immediate reduction of odor was noticed in the residence. After 16 hours, there were no odors emanating from the pump or the seepage field. Moreover, the bio-solid crust was digested. To conclude treatment of the system, a further inoculation of 500 ml of the concentrated composition of Example 1 was conducted after 8 weeks.

Alternative methods for the treatment of septic sludge may include a feed and grow activation prior to treatment; this may include additional molasses or another carbon source

Example 8

Soil Testing on Golf Turf Increased Phosphate Content

On a golf green, half of the green was treated one time per week with IN-M1, Accession No. PTA-12383 ($3.8\times10^9$ cells per L in chlorine free water for 5 weeks and the green was included in the standard turf management program of the course. The green was treated as normally treated with chemical fertilizers and pesticides. A soil analysis was performed for the treated half (treated with Inocul-M) and the untreated half.

| Phosphate | Untreated | 82 ppm | |
| | Treated | 117 ppm | 30% |
| Potassium | Untreated | 65 ppm | |
| | Treated | 70 ppm | 7.11% |
| Magnesium | Untreated | 78 ppm | |
| | Treated | 86 ppm | 9.3% |

Measurements taken after treatment with a microorganism-containing composition, IN-M1, Accession No. PTA-12383 showed an increase in phosphate in the soil.

Example 10

Treatment of Wastes and removal of Coliforms

This study was designed to monitor effects on coliform contamination of septic sludge from city municipality waste water treatment plant with IN-M1 at $1\times10^6$ cells/mL and to monitor a wide range of endpoints including coliform, toxic chemical and organic compounds. It was found that there was a significant reduction in coliform presence (measured as cfu/100 mL, colony forming units), from 8.3 million cfus to 100 000 cfus/100 ml, following 7 days of treatment. The entire treatment period was 22 days. There was an increase in nitrate concentration which indicates an increase in nutritional value of the biosolids as a soil amendment for agricultural purposes. There was a trend in reduction of mercury concentration and change in toluene concentration.

Protocol Per Cubic Meter Septic Sludge 0.1 L concentrate for example; IN-M1 at $1\times10^6$ cells/mL, +0.2 L molasses+0.75 L water per $m^3$ sludge were combined together. The mixture was allowed to stand at ambient temperature for 48 hours. The mixture was thoroughly combined with a 2-4% septic sludge and water in the lagoon or settling tank of approximately 2000 liters. In the case of separated high percentage septic sludge, the sample should be mixed very thoroughly making sure that the product is distributed throughout to avoid pockets where pathogens can grow. The lagoon was left alone for 2-6 weeks.

Though not wishing to be bound by any particular theory, in a water mixture, the bio-solids gradually diminished in quantity, and it is thought that the beneficial microbes colonized the water and sediment and dissolved the organic matter; at the same time the pre-biotics and signaling peptides stimulated the indigenous flora to also breakdown the organic material.

Figure 4:
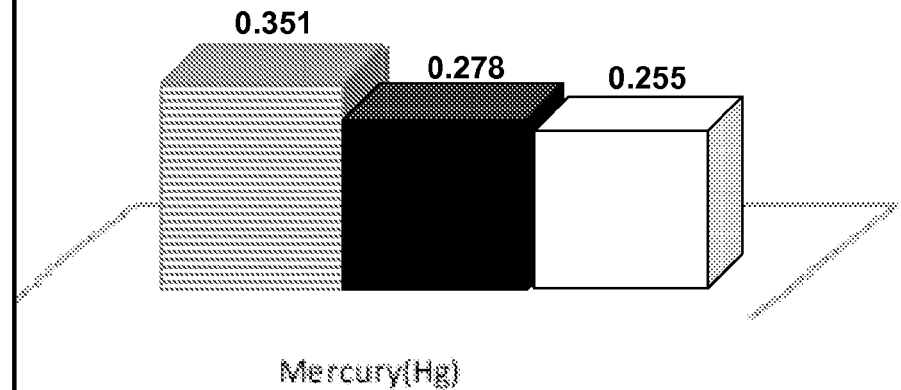
FIG. 4 is a graph showing mercury levels in a site after treatment with a composition of the present invention.

In another instance coli-form bacteria replication was inhibited by the addition of 0.1 L of a concentrated solution of IN-M1, +0.2 L molasses+0.75 L water per $m^3$ sludge were combined together and left to ferment at ambient temperature 22 days. The composition may contain species which sequester nitrogen both from volatile organic compounds (VOCs) and the air and convert it into soluble forms. See FIG. 4.

| Sample | Day 0 | Day 7 | Day 22 | Detection limit |
|---|---|---|---|---|
| Coliforms (cfu/100 mL) | $8.2 \times 10^6$ | $4.3 \times 10^5$ | $1.0 \times 10^5$ | 1 |
| Ammonia mg/L | 870 | 360 | 421 | 5 |
| Nitrate | 0.5 | 32.1 | $1.32 \times 10^4$ | 0.5 |
| Mercury | 0.351 | 0.278 | 0.255 | 0.05 |
| Toluene mg/L | 0.432 | 0.244 | 0.373 | 0.005 |

Figure 3:
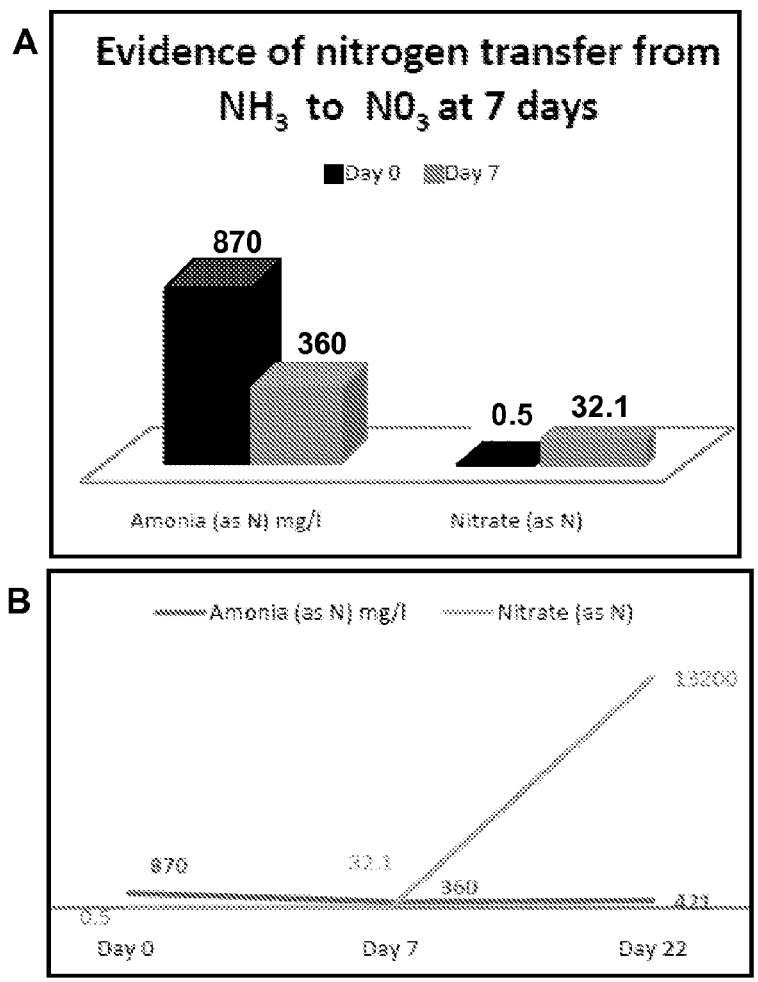
FIGS. 3 A and B are graphs showing nitrogen transfer (A) and nitrate increase (B) in a site after treatment with a composition of the present invention.
Figure 5:
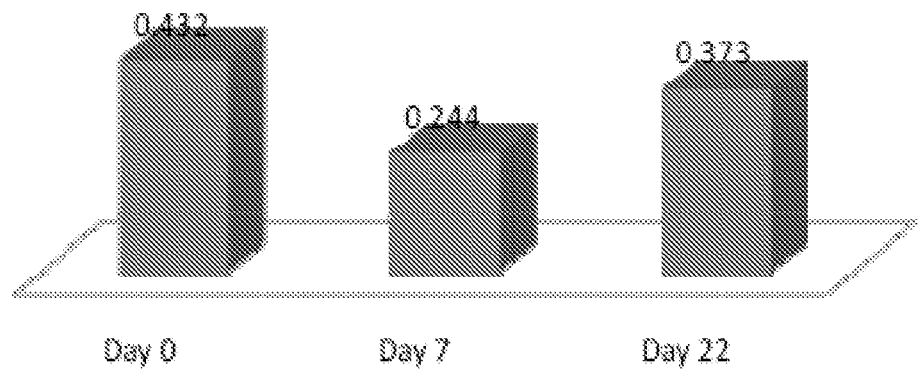
FIG. 5 is a graph showing toluene levels in a site after treatment with a composition of the present invention.

The decrease in ammonia bound nitrogen decreased by 58.6% day 7 to 51.6% day 22; nitrate bound levels increased more than 6000 times by treatment day 7 to approximately 2.6 million times by day 22. This may be evidence of either transfer of nitrogen from volatile form (ammonia) to soluble form (nitrates) and/or the sequestering of nitrogen to a soluble form from the air, through the action of nitrogen fixing microbes in the formulation. The treatment may enhance the rapid conversion of nitrogen to soluble forms which may be used as a soil amendment. It is thought that the relative nitrogen mass difference is due to the fact the fermentation parameters are anoxic. See FIGS. 3A and B. See FIGS. 4 and 5 for mercury and toluene results.

The invention claimed is:

1. A method of increasing growth of a plant, comprising,
   (a) applying to the foliage of a plant or to a plant growing medium an effective amount of a composition consisting of fermentation broth and microorganisms consisting of isolated microorganisms of IN-M1, Accession No. PTA-12383,
   so that a treated plant has increased growth compared to an untreated plant.

2. The method of claim 1, wherein applying to the foliage of a plant comprises applying the composition to the seeds, roots, or leaves and stalks of plants, or a combination thereof.

3. The method of claim 1, wherein the plant is grown in a field or outside, in vertical farming, in aeroponic conditions, under hydroponic conditions, or combined hydroponic and aeroponic conditions.

4. The method of claim 1, wherein the increased plant growth is increased yield per plant of treated plants is increased compared to untreated plants.

5. The method of claim 1, wherein the increased plant growth is increased biomass of treated plants compared to untreated plants.

6. The method of claim 1, wherein the increased plant growth is increased fruit production of treated plants compared to untreated plants.

7. The method of claim 1, wherein the increased plant growth is increased production period of treated plants compared to untreated plants.

8. The method of claim 1, wherein the increased plant growth is increased productive lifespan of treated plants compared to untreated plants.

9. The method of claim 1, wherein the increased plant growth is increased is associated with reduced insect infestation of treated plants compared to untreated plants.

10. The method of claim 2, wherein the increased plant growth is increased seed germination of treated seeds compared to untreated seeds.

11. A method of increasing growth of a plant, comprising,
    (a) applying to the foliage of a plant or to a plant growing medium an effective amount of a composition consisting of fermentation broth and microorganisms consisting of isolated microorganisms of IN-M1, Accession No. PTA-12383, and *Candida utilis, Streptococcus lactis, Lactobacillus planterum*, or a micorrhyzal fungus, or combination thereof;
    so that a treated plant has increased growth compared to an untreated plant.

12. A method of increasing growth of a plant, comprising,
    (a) applying to the foliage of a plant or to a plant growing medium an effective amount of a composition consisting of fermentation broth and microorganisms consisting of isolated microorganisms of IN-M1, Accession No. PTA-12383; so that a treated plant has increased growth compared to an untreated plant;
    wherein the composition is prepared using an initial mixed culture inoculated with a first mixed culture of isolated microorganisms consisting of *Lactobacillus helveticus*, IN-LH1, Accession No. PTA-12386, *Bacillus subtilis*, IN-BS1, Accession No. PTA-12385, and *Lactobacillus casei*; a second mixed culture of isolated microorganisms consisting of *Saccharomyces cerevisiae*, IN-SC1, Accession No. PTA-12384, and *Rhodopseudomonas palustris*, IN-RP1, Accession No, PTA-12387; and a third mixed culture of isolated microorganisms consisting of *Saccharomyces cerevisiae*, IN-SC1, Accession No. PTA-12384, and *Aspergillus oryzae*; and
    wherein the first mixed culture, second mixed culture, and third mixed culture are added to the initial mixed culture at a ratio to each other of 1:1:0.5.

* * * * *